(12) United States Patent
Lee

(10) Patent No.: US 12,339,143 B2
(45) Date of Patent: Jun. 24, 2025

(54) TACTILE SENSOR EQUIPPED WITH MULTIPLE LIGHT SOURCES AND A PHOTO DETECTOR, SENSING DEVICE AND ROBOT HAVING THE SAME

(71) Applicant: Tencent Technology (Shenzhen) Company Limited, Shenzhen (CN)

(72) Inventor: Wangwei Lee, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 0 days.

(21) Appl. No.: 18/197,476

(22) Filed: May 15, 2023

(65) Prior Publication Data

US 2023/0288229 A1 Sep. 14, 2023

Related U.S. Application Data

(63) Continuation of application No. PCT/CN2022/124575, filed on Oct. 11, 2022.

(30) Foreign Application Priority Data

Dec. 17, 2021 (CN) .......................... 202111551931.7

(51) Int. Cl.
*G01D 5/28* (2006.01)
*B25J 13/08* (2006.01)
(Continued)

(52) U.S. Cl.
CPC ............ *G01D 5/285* (2013.01); *B25J 13/084* (2013.01); *B25J 19/021* (2013.01); *G01D 5/30* (2013.01); *G01L 1/24* (2013.01); *G01L 5/228* (2013.01)

(58) Field of Classification Search
CPC ......... B25J 13/084; B25J 19/021; G01D 5/30; G01D 5/285; G01L 5/166; G01L 5/228; G01L 1/24; A61F 2/10
See application file for complete search history.

(56) References Cited

U.S. PATENT DOCUMENTS 8,411,140 B2 4/2013 Adelson
9,513,178 B2 12/2016 Tar et al.
(Continued)

FOREIGN PATENT DOCUMENTS

CN 106052914 A * 10/2016
CN 108814769 A 11/2018
(Continued)

OTHER PUBLICATIONS

Tencent Technology, ISR, PCT/CN2022/124575, Dec. 29, 2022, 3 pgs.

(Continued)

*Primary Examiner* — Jennifer D Bennett
*Assistant Examiner* — Erin R Garber
(74) *Attorney, Agent, or Firm* — Morgan, Lewis & Bockius LLP

(57) ABSTRACT

This application discloses a tactile sensor, a detection method for a touch event, a sensing device and a robot, and belongs to the field of sensor design. The tactile sensor includes: a sensing unit, an elastomer support housing and a base; the sensing unit is disposed in an inner cavity enclosed by the elastomer support housing and the base; and the sensing unit includes at least two light sources, a photo detector and a reflector, where the photo detector is disposed on base, the at least two light sources are disposed around the periphery of the photo detector on the base, and the reflector is disposed at the top of an inner cavity of the elastomer support housing. By adopting the combination of (Continued)

a plurality of light sources and one photo detector, the number of photo detectors for use is reduced, so that the volume of the tactile sensor is reduced.

7 Claims, 17 Drawing Sheets

(51) Int. Cl.
  *B25J 19/02* (2006.01)
  *G01D 5/30* (2006.01)
  *G01L 1/24* (2006.01)
  *G01L 5/22* (2006.01)

(56) References Cited

U.S. PATENT DOCUMENTS

| | | | |
|---|---|---|---|
| 10,481,262 B1 | 11/2019 | DeSalvo et al. | |
| 2011/0243701 A1* | 10/2011 | Kiyose | B25J 13/088 356/615 |
| 2014/0326882 A1* | 11/2014 | Tar | G01L 1/248 250/338.1 |
| 2017/0363464 A1* | 12/2017 | Shafer | G01D 5/30 |
| 2018/0106692 A1 | 4/2018 | Ciocarlie et al. | |
| 2020/0281713 A1 | 9/2020 | Li | |
| 2021/0299886 A1 | 9/2021 | Alspach et al. | |
| 2022/0397469 A1* | 12/2022 | Katsuhara | H05K 1/181 |

FOREIGN PATENT DOCUMENTS

| | | |
|---|---|---|
| CN | 109724651 A | 5/2019 |
| CN | 111661815 A | 9/2020 |
| CN | 112105900 A | 12/2020 |
| KR | 102059593 B1 | 2/2020 |
| WO | WO 2020240202 A1 | 12/2020 |

OTHER PUBLICATIONS

Tencent Technology, WO, PCT/CN2022/124575, 29DEC2022, 5 pgs.

Tencent Technology, IPRP, PCT/CN2022/124575, Jun. 13, 2024, 6 pgs.

Tencent Technology, Extended European Search Report, EP Patent Application No. 22906028.0, Dec. 16, 2024, 9 pgs.

* cited by examiner

US 12,339,143 B2

TACTILE SENSOR EQUIPPED WITH MULTIPLE LIGHT SOURCES AND A PHOTO DETECTOR, SENSING DEVICE AND ROBOT HAVING THE SAME

CROSS-REFERENCE TO RELATED APPLICATIONS

This application is a continuation application of PCT Patent Application No. PCT/CN2022/124575, entitled "TACTILE SENSOR, DETECTION METHOD FOR TOUCH EVENT, SENSING DEVICE AND ROBOT" filed on Oct. 11, 2022, which claims priority to Chinese Patent Application No. 202111551931.7, filed with the China National Intellectual Property Administration on Dec. 17, 2021, and entitled "TACTILE SENSOR, DETECTION METHOD FOR TOUCH EVENT, SENSING DEVICE AND ROBOT", all of which is incorporated herein by reference in its entirety.

FIELD OF THE TECHNOLOGY

Embodiments of this application relate to the field of sensor design, in particular to a tactile sensor, a detection method for a touch event, a sensing device and a robot.

BACKGROUND OF THE DISCLOSURE

With the rapid development and extensive application of robot technology, robots are expected to not only complete set mechanical motion, but also sense the contact force acting between it and the external environment. Therefore, tactile sensors are usually combined with robots.

In related technologies, an optics-based displacement sensor is provided with a plurality of photo detectors (PDs) and a single light source to detect light density distribution, thus deducing the displacement of a sensing surface of the displacement sensor and further calculating the magnitude and direction of force exerted on the displacement sensor.

However, the optics-based displacement sensor in the related technology occupies a relatively large space and is higher in cost, given that the optics-based displacement sensor is provided with a plurality of PDs which are large in size and each has a special amplifying circuit.

SUMMARY

This application provides a tactile sensor, a detection method for a touch event, a sensing device and a robot. The tactile sensor is smaller in size, easy to build and less costly. The technical solutions are as follows:

According to one aspect of this application, a tactile sensor is provided, including: a sensing unit, an elastomer support housing and a base; where
    the sensing unit is disposed in an inner cavity enclosed by the elastomer support housing and the base; and
    the sensing unit includes at least two light sources, a photo detector and a reflector, where the photo detector is disposed on the base, the at least two light sources are disposed around the periphery of the photo detector on the base, and the reflector is disposed at the top of an inner cavity of the elastomer support housing.

According to another aspect of this application, a detection method for a touch event is provided, the detection method being executed by a computer device and including:
    acquiring light intensity measured by a photo detector in the tactile sensor; and
    measuring at least one of the magnitude and direction of force exerted on the tactile sensor based on the light intensity.

According to another aspect of this application, an electronic skin is provided, the electronic skin including:
    a tactile sensor array covering the electronic skin and including at least two foregoing tactile sensors.
    including:

According to another aspect of this application, a robot is provided, the robot
    the foregoing tactile sensor or the foregoing electronic skin covering the robot at a preset position.

According to another aspect of this application, a sensing device is provided, the sensing device including:
    at least one foregoing tactile sensor and a controller connected to the tactile sensor and executed to implement the foregoing detection method for a touch event.

According to another aspect of this application, a computer-readable storage medium is provided, the storage medium storing at least one instruction, the at least one instruction being loaded and executed by a processor to implement the foregoing detection method for a touch event.

According to another aspect of this application, a computer program product is provided, the computer program product including a computer program/instruction, the computer program/instruction, when executed by a processor, implementing the foregoing detection method for a touch event.

The technical solutions provided in this application achieve at least the following beneficial effects:
    the photo detector is disposed on the base, the at least two light sources are disposed around the periphery of the photo detector on the base, and the reflector is disposed at the top of an inner cavity of the elastomer support housing. By adopting the combination of a plurality of light sources and one photo detector for the tactile sensor in this application, the number of photo detectors for use is reduced, so that the tactile sensor has a decreased volume and is less costly. In the meanwhile, with the reduction in the number of photo detectors, readout circuits special for the photo detector are reduced accordingly, which makes the tactile sensor simpler in structure and faster in measurement speed.

BRIEF DESCRIPTION OF THE DRAWINGS

To describe the technical solutions in the embodiments of this application more clearly, the drawings required to describe the embodiments are briefly described below. Apparently, the drawings described below are only some embodiments of this application. A person skilled in the art may further obtain other drawings based on these drawings without creative efforts.

DESCRIPTION OF EMBODIMENTS

To make the objective, technical solutions, and advantages of this application clearer, embodiments of this application will be further described in detail with reference to the accompanying drawings.

Figure 1:
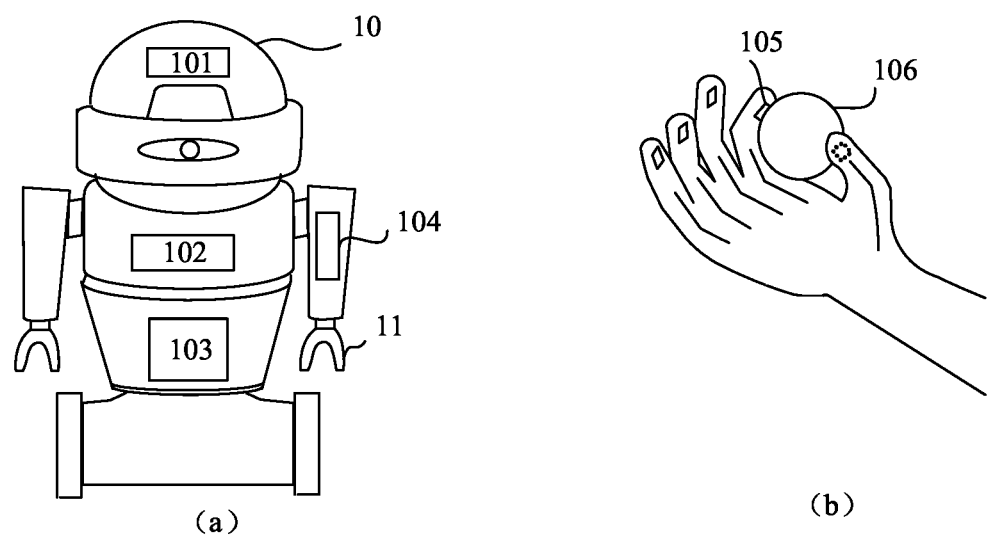
FIG. 1 is a schematic structural diagram of a tactile sensing system according to an exemplary embodiment of this application.

FIG. 1 is a schematic structural diagram of a tactile sensing system according to an exemplary embodiment of this application. The tactile sensing system 100 includes an intelligent robot 10, a tactile sensor 101, a tactile sensor 102, a tactile sensor 103 and a tactile sensor 104, where the plurality of tactile sensors are attached to the intelligent robot 10. As shown in FIG. 1(a), the tactile sensor according to this embodiment of this application is flexible and may be attached to an outer surface of the intelligent robot 10 to thus form an "electronic skin". The outer surface of the intelligent robot 10 to which the tactile sensor is attached may be of any shape, such as a sphere, a hemisphere, a cylinder, an irregular shape, etc. Schematically, as shown in FIG. 1(a), the tactile sensor 101 is attached to the head of the intelligent robot 10, the tactile sensor 102 is attached to the chest of the intelligent robot, the tactile sensor 103 is attached to the abdomen of the intelligent robot, and the tactile sensor 104 is attached to the arm of the intelligent robot.

The tactile sensor may also be attached to a manipulator 11 of the intelligent robot. As shown in FIG. 1(b), the tactile sensor 105 is attached to a finger of the manipulator 11 and makes contact with a target object through the manipulator 11, which can provide torque feedback to determine the gesture for grabbing the target object and how much force it takes to grab the target object. If the object 106 to be grabbed by the manipulator 11 is a sphere, then the manipulator 11 grabs the object 106 using the gesture shown in FIG. 1(b). In a possible implementation, the tactile sensor 105 may be attached to the fingertip part or knuckle part of the finger, the palm or the whole hand, which is not limited in this application.

Figure 2:
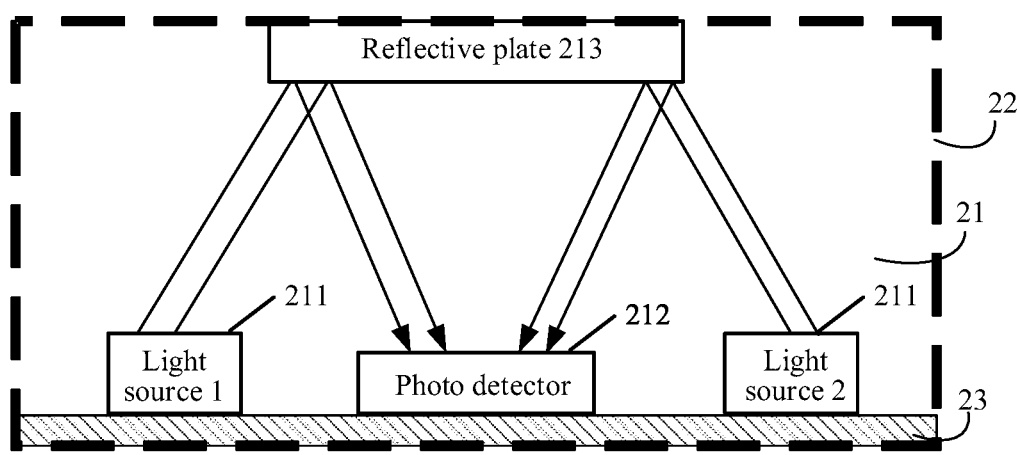
FIG. 2 is a schematic structural diagram of a tactile sensor according to an exemplary embodiment of this application.

FIG. 2 shows a schematic structural diagram of a profile of a tactile sensor according to an exemplary embodiment of this application. The tactile sensor includes: a sensing unit 21, an elastomer support housing 22 and a base 23.

The sensing unit 21 is disposed in an inner cavity enclosed by the elastomer support housing 22 and the base 23.

The sensing unit 21 includes at least two light sources 211, a photo detector 212 and a reflector 213, where the photo detector 212 is disposed on base 23, the at least two light sources 211 are disposed around the periphery of the photo detector 212 on the base 23, and the reflector 21 is disposed at the top of an inner cavity of the elastomer support housing 22. For example, FIG. 2 shows at least two light sources 211 including a light source 1 and a light source 2.

In a possible implementation, the reflector 213 may specifically be, but not limited to, at least one of a reflective plate, a reflective block, and a reflective film, which is not limited in the embodiments of this application.

In a possible implementation, the sensing unit 21 includes eight light sources 211. The photo detector 212 is disposed on the base 23, and the eight light sources 211 are symmetrically disposed around the periphery of the photo detector 212 on the base 23.

Figure 3:
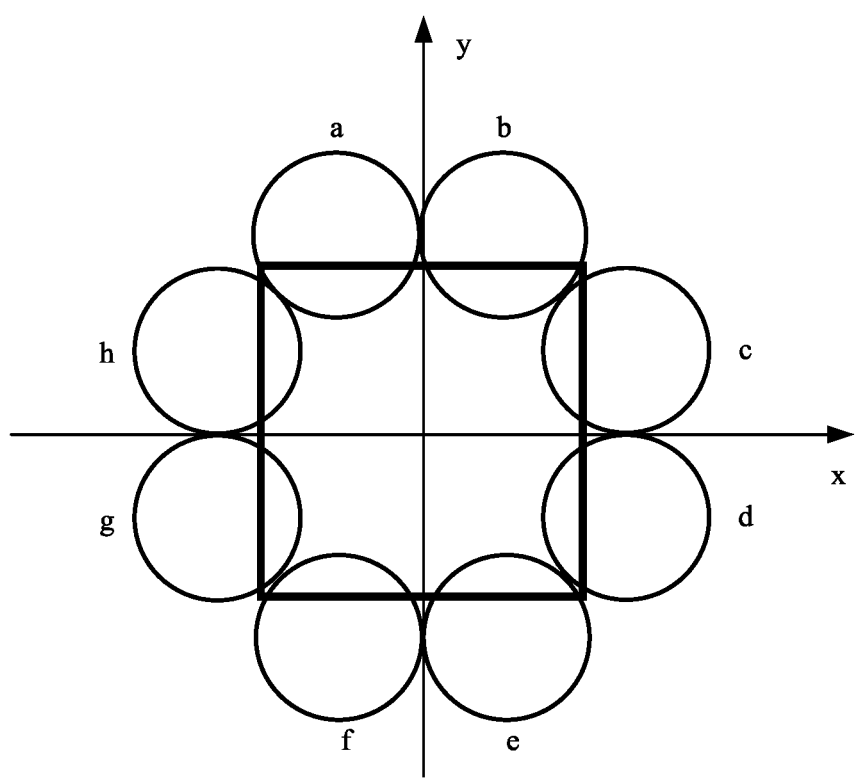
FIG. 3 is a schematic diagram of light intensity measured by a tactile sensor according to an exemplary embodiment of this application.

FIG. 3 shows a schematic diagram of light intensity measured by a tactile sensor according to an exemplary embodiment of this application. The circle in FIG. 3 represents the illumination range of each of the eight light sources 211, and the box represents a reflector 213 at the top of the inner cavity of the elastomer support housing 22. The eight light sources 211 include a light source a, a light source b, a light source c, a light source d, a light source e, a light source f, a light source g and a light source h, respectively, and the eight light sources 211 are disposed around the periphery of the photo detector 212 on the base 23. The light source a and the light source b are disposed on both sides of the positive half axis of the y-axis; the light source c and the light source d are disposed on both sides of the positive half axis of the x-axis; the light source e and the light source f are disposed on both sides of the negative half axis of the y-axis; and the light source g and the light source h are disposed on both sides of the negative half axis of the x-axis. The light source a is a first positive y-axis light source, and the light source b is a second positive y-axis light source; the light source c is a first positive x-axis light source, and the light source d is a second positive x-axis light source; the light source e is a first negative y-axis light source, and the light source f is a second negative y-axis light source; and the light source g is a first negative x-axis light source, and the light source h is a second negative x-axis light source.

Exemplarily, the upper surface of the elastomer support housing 22 is offset when force is applied to the elastomer support housing 22, thereby driving the reflector 213 at the top of the inner cavity of the elastomer support housing 22 to be offset, which further results in a change in the light intensity of reflected light received by the photo detector 212. The on/off of the light sources 211 are controlled in turn, and the photo detector 212 measures the light intensity of the reflected light of each of the light sources 211. By calculating the changes in the light intensity of the reflected light of each of the light sources 211, the displacement of the reflector 213 at the top of the inner cavity of the elastomer support housing 22 is calculated, and then the magnitude and direction of the force exerted on the tactile sensor are acquired.

The upper surface of the elastomer support housing 22 is offset when force in a direction of translation is exerted on the tactile sensor (e.g., when force in a direction of translation along the x-axis is exerted on the tactile sensor), thereby driving the reflector 213 at the top of the inner cavity of the elastomer support housing 22 to be offset along the x-axis, which further results in a change in the light intensity of reflected light received by the photo detector 212. The on/off of the light source c and light source h are controlled in turn, and the photo detector 212 measures the light intensity of the reflected light of the light source c and light source h. By calculating the changes in the light intensity of the reflected light of each of the light source c and light source h, the displacement of the reflector 213 at the top of the inner cavity of the elastomer support housing 22 along the x-axis is calculated, and then the magnitude and direction of the force exerted on the tactile sensor are acquired.

The upper surface of the elastomer support housing 22 rotates when force in a direction of rotation is exerted on the tactile sensor (e.g., force in a direction of rotation about the x-axis is exerted on the tactile sensor), thereby driving the reflector 213 at the top of the inner cavity of the elastomer support housing 22 to rotate about the x-axis, which further results in a change in the light intensity of reflected light received by the photo detector 212. The on/off of the light source g and light source h are controlled in turn, and the photo detector 212 measures the light intensity of the reflected light of each of the light source g and light source h. By calculating the changes in the light intensity of the reflected light of each of the light source g and light source h, the displacement or angle of the reflector 213 at the top of the inner cavity of the elastomer support housing 22 in a direction of rotation about the x-axis is calculated, and then the magnitude and direction of the force exerted on the tactile sensor are obtained.

To sum up, by adopting the combination of a plurality of light sources and one photo detector for the tactile sensor in this embodiment, the number of photo detectors for use is reduced, so that the volume of the tactile sensor is reduced. In the meanwhile, with the reduction in the number of photo detectors, readout circuits special for the photo detector are reduced accordingly, which makes the tactile sensor simpler in structure and faster in measurement speed.

The tactile sensor, when subject to force in a direction of translation, measures the light intensity of the reflected light of the light sources corresponding to the positive half axis and negative half axis in a direction of translation. By calculating the changes in the light intensity of the reflected light of the light sources corresponding to the positive half axis and negative half axis in a direction of translation, the magnitude and direction of the force exerted on the tactile sensor in a direction of translation are sensed.

The tactile sensor, when subject to force in a direction of rotation, measures the light intensity of the reflected light of the light sources on both sides of a rotation axis. By calculating the changes in the light intensity of the reflected light of the light sources on both sides of the rotation axis, the magnitude and direction of the force exerted on the tactile sensor in a direction of rotation are sensed.

The tactile sensor in the embodiment measures the light intensity of the reflected light of each of the light sources through a plurality of light sources and a photo detector, thus sensing the magnitude and direction of force in six degrees of freedom, such as a direction of translation and a direction of rotation.

Based on the embodiment in FIG. 2, the force in a direction of translation and direction of rotation measured by the tactile sensor is described in detail below.

Figure 4:
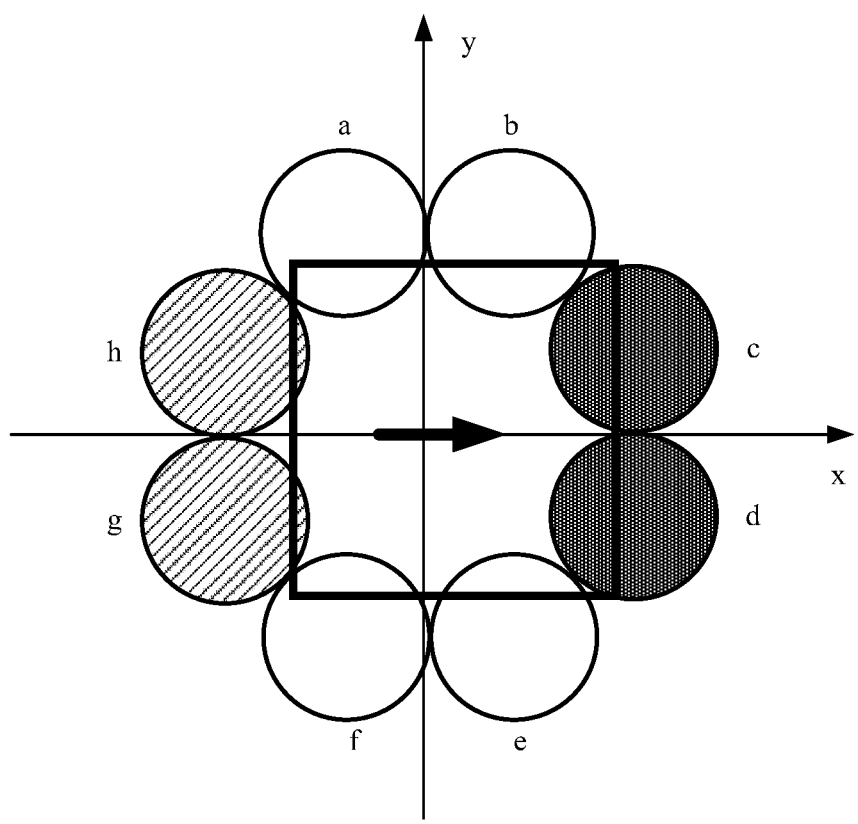
FIG. 4 is a schematic diagram of light intensity of reflected light measured by a photo detector in case a force in the positive direction of the x-axis is exerted on the tactile sensor according to an exemplary embodiment of this application.

Exemplarily, FIG. 4 shows a schematic diagram of light intensity of reflected light measured by a photo detector in case a force in a direction of translation along the x-axis is exerted on the tactile sensor.

In case force in a direction of translation along the x-axis is exerted on the tactile sensor, the reflector 213 at the top of the inner cavity of the elastomer support housing 22 is displaced along the x-axis. As a result, the overall light intensity of the reflected light of the light source c and light source d measured by the photo detector 212 increases, while the overall light intensity of the reflected light of the light source h and light source g measured by the photo detector 212 decreases.

Exemplarily, in case a force along the x-axis is exerted on the tactile sensor, the positive x-axis light source is turned on, and the light intensity of the positive x-axis light source measured by the photo detector is acquired when the positive x-axis light source is in the "on" state; and the negative x-axis light source is turned on, and the light intensity of the negative x-axis light source measured by the photo detector is acquired when the negative x-axis light source is in the "on" state; where the first difference value indicates a difference between the light intensity of the positive x-axis light source measured by the photo detector 212 and the light intensity of the negative x-axis light source measured by the photo detector 212. The first mapping relation may indicate a correspondence between the magnitude and direction of force exerted on the tactile sensor in a direction of translation and changes in the light intensity measured by the photo detector.

For example, in case a force along the x-axis is exerted on the tactile sensor, first, the light source c and the light source d are turned on, and the overall light intensity (λc+λd) of reflected light of the light source c and the light source d is measured using the photo detector 212. Then, the light source c and the light source d are turned off, the light source h and the light source g are turned on, and the overall light intensity (λh+λg) of reflected light of the light source h and the light source g is measured using the photo detector 212. By measuring the difference between the light intensity (λc+λd) and the light intensity (λh+λg), the displacement produced by the reflector 213 at the top of the inner cavity of the elastomer support housing 22 along the x-axis is obtained, and then the magnitude and direction of the force applied to the elastomer support housing 22 are obtained. For example, in case a force along the x-axis is exerted on the tactile sensor, the correspondence between the displacement transx produced by the reflector 213 of the tactile sensor along the x-axis and the light intensity measured by the photo detector 212 can be expressed as follows:

$$trans_x \propto \frac{(\lambda_c + \lambda_d) - (\lambda_h + \lambda_g)}{\lambda_c + \lambda_d + \lambda_h + \lambda_g}$$

λc represents the light intensity of reflected light of the light source c measured by the photo detector; λd represents the light intensity of reflected light of the light source d measured by the photo detector; λh represents the light intensity of reflected light of the light source h measured by the photo detector; and λg represents the light intensity of reflected light of the light source g measured by the photo detector.

It may be understood that, the magnitude and direction of the force on the x-axis can be measured based on the overall light intensity of the reflected light of the light source c and the light source d and the overall light intensity of the reflected light of the light source h and the light source g. In a possible implementation, the overall light intensity is at least one of the average light intensity of the reflected light of the light source c and the light source d, the sum of the light intensity of the reflected light of the light source c and the light source d, and a weighted value of the light intensity of the reflected light of the light source c and the light source d, which is not limited in the embodiments of this application. Alternatively, when the magnitude and direction of the force along the x-axis are to be measured, it is possible to conduct measurement by selecting two light sources on the x-axis, including but not limited to light source c and light source h, or light source d and light source g, or light source c and light source g, which is not limited in the embodiments of this application.

That is, in case the light source c and the light source h are measured, the correspondence between the displacement transx produced by the reflector 213 of the tactile sensor along the x-axis and the light intensity measured by the photo detector 212 can be expressed as follows:

$$trans_x \propto \frac{\lambda_c - \lambda_h}{\lambda_c + \lambda_h}$$

In case the light source d and the light source g are measured, the correspondence between the displacement transx produced by the reflector 213 of the tactile sensor along the x-axis and the light intensity measured by the photo detector 212 can be expressed as follows:

$$trans_x \propto \frac{\lambda_d - \lambda_g}{\lambda_d + \lambda_g}$$

In case the light source C and the light source g are measured, the correspondence between the displacement transx produced by the reflector 213 of the tactile sensor along the x-axis and the light intensity measured by the photo detector 212 can be expressed as follows:

$$trans_x \propto \frac{\lambda_c - \lambda_g}{\lambda_c + \lambda_g}$$

Exemplarily, Table 1 (reference table of first mapping relation) shows a correspondence between the magnitude and direction of force exerted on the tactile sensor in a direction of translation and changes in the light intensity measured by the photo detector.

TABLE 1

Reference table of first mapping relation

| Position of light source to be tested | Measured light intensity/ Lux | Translational displacement/ mm | Magnitude of force/N | Direction of force | Magnitude of resultant force/N | Direction of resultant force |
|---|---|---|---|---|---|---|
| Light source c | X1 | Y1 | 3 | Positive direction of the x-axis | 5 | Making an angle of 45° with the positive direction of the x- |
| Light source h | X2 | | | | | |
| Light source e | X3 | Y2 | 4 | Positive direction of the y- | | |
| Light | X4 | | | | | |

TABLE 1-continued

Reference table of first mapping relation

| Position of light source to be tested | Measured light intensity/ Lux | Translational displacement/ mm | Magnitude of force/N | Direction of force | Magnitude of resultant force/N | Direction of resultant force |
|---|---|---|---|---|---|---|
| source b | | | | axis | | axis |
| Light source a | Default value | 0 | 0 | | | |
| Light source d | Default value | 0 | 0 | | | |
| Light source f | Default value | 0 | 0 | | | |
| Light source g | Default value | 0 | 0 | | | |

As shown in Table 1, in case a force in a direction of translation is exerted on the tactile sensor, the light intensity of the reflected light of each of the light sources at a specific position is measured, or the light intensity of the reflected light of all the light sources is measured. For example, in case a force in a direction of translation is exerted on the tactile sensor, the light intensity of the reflected light of all the light sources is measured to obtain the light intensity X1, light intensity X2, light intensity X3 and light intensity X4 corresponding to light source c, light source h, light source e and light source b, respectively. As can be seen from the correspondence between the displacement transx produced by the reflector 213 of the tactile sensor along the x-axis and the light intensity measured by the photo detector 212, the reflector 213 at the top of the inner cavity of the elastomer support housing 22 produces a translational displacement of Y1 along the x-axis, and the reflector 213 at the top of the inner cavity of the elastomer support housing 22 produces a translational displacement of Y2 along the y-axis. Further, it is obtained that the magnitude of force applied to the elastomer support housing 22 along the x-axis is 3N, and the magnitude of force applied to the elastomer support housing 22 along the y-axis is 5N. Finally, it is obtained that: the force exerted on the tactile sensor in a direction of translation has a magnitude of 5N, and makes an angle of 45 with the positive direction of the x-axis.

Figure 5:
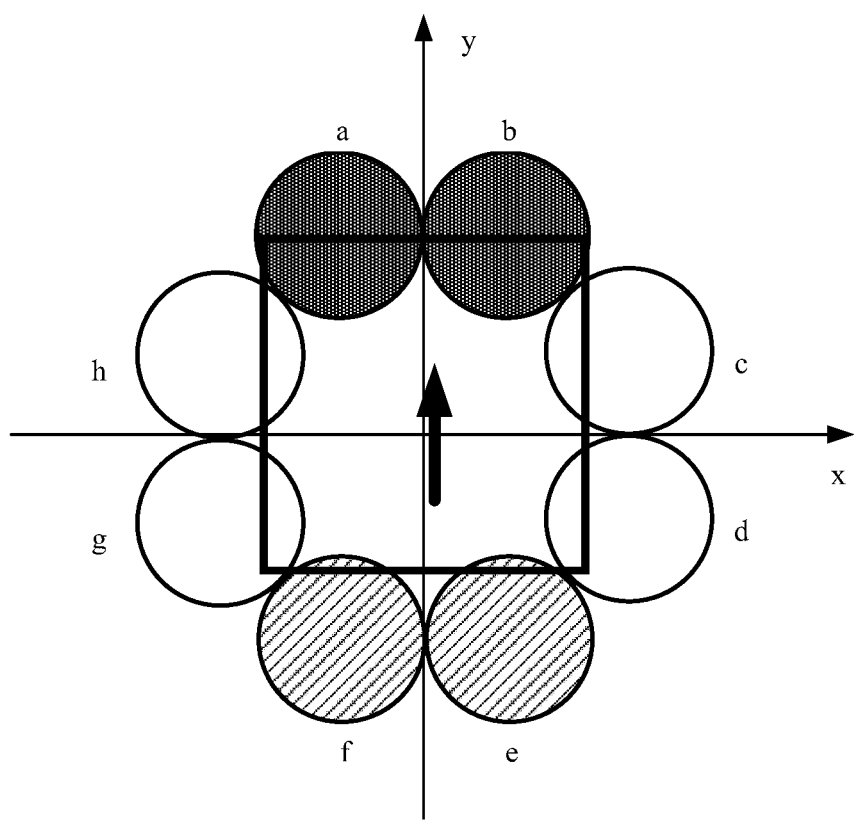
FIG. 5 is a schematic diagram of light intensity of reflected light measured by a photo detector in case a force in the positive direction of the y-axis is exerted on the tactile sensor according to an exemplary embodiment of this application.

Exemplarily, FIG. 5 shows a schematic diagram of light intensity of reflected light measured by a photo detector in case a force in the positive direction of the y-axis is exerted on the tactile sensor, in case a force along the y-axis is exerted on the tactile sensor, the reflector 213 at the top of the inner cavity of the elastomer support housing 22 is offset along the y-axis. As a result, the overall light intensity of the reflected light of the light source a and light source b measured by the photo detector 212 increases, while the overall light intensity of the reflected light of the light source f and light source e measured by the photo detector 212 decreases.

In case force in a direction of translation along the y-axis is exerted on the tactile sensor, the positive y-axis light source is turned on, and the light intensity of the positive y-axis light source measured by the photo detector 212 is acquired when the positive y-axis light source is in the "on" state; the negative y-axis light source is turned on, and the light intensity of the negative y-axis light source measured by the photo detector 212 is acquired when the negative y-axis light source is in the "on" state; and the magnitude and direction of force exerted on the tactile sensor in a direction of translation along the y-axis in the touch event are acquired according to a second difference value and the first mapping relation; where the second difference value may indicate a difference between the light intensity of the positive y-axis light source measured by the photo detector 212 and the light intensity of the negative y-axis light source measured by the photo detector 212.

For example, first, the light source a and the light source b are turned on, and the overall light intensity ($\lambda a+\lambda b$) of reflected light of the light source a and the light source b is measured using the photo detector 212. Then, the light source a and the light source b are turned off, the light source e and the light source f are turned on, and the overall light intensity ($\lambda e+\lambda f$) of reflected light of the light source e and the light source f is measured using the photo detector 212. By measuring the difference between the light intensity ($\lambda a+\lambda b$) and the light intensity ($\lambda e+\lambda f$), the displacement produced by the reflector 213 at the top of the inner cavity of the elastomer support housing 22 along the y-axis is obtained, and then the magnitude of the force applied to the elastomer support housing 22 is obtained. For example, in case a force in a direction of translation along the y-axis is exerted on the tactile sensor, the correspondence between the displacement transy produced by the reflector of the tactile sensor along the y-axis and the light intensity measured by the photo detector 212 can be expressed as follows:

$$trans_y \propto \frac{(\lambda_a + \lambda_b) - (\lambda_e + \lambda_f)}{\lambda_a + \lambda_b + \lambda_e + \lambda_f}$$

$\lambda a$ represents the light intensity of reflected light of the light source a measured by the photo detector; $\lambda b$ represents the light intensity of reflected light of the light source b measured by the photo detector; $\lambda e$ represents the light intensity of reflected light of the light source e measured by the photo detector; and $\lambda f$ represents the light intensity of reflected light of the light source f measured by the photo detector.

It may be understood that, when the magnitude and direction of the force along the y-axis are to be measured, it is possible to conduct measurement by selecting two light sources on the y-axis, including but not limited to light source a and light source f, or light source a and light source e, or light source b and light source f, or light source b and light source e, which is not limited in the embodiments of this application.

Figure 6:
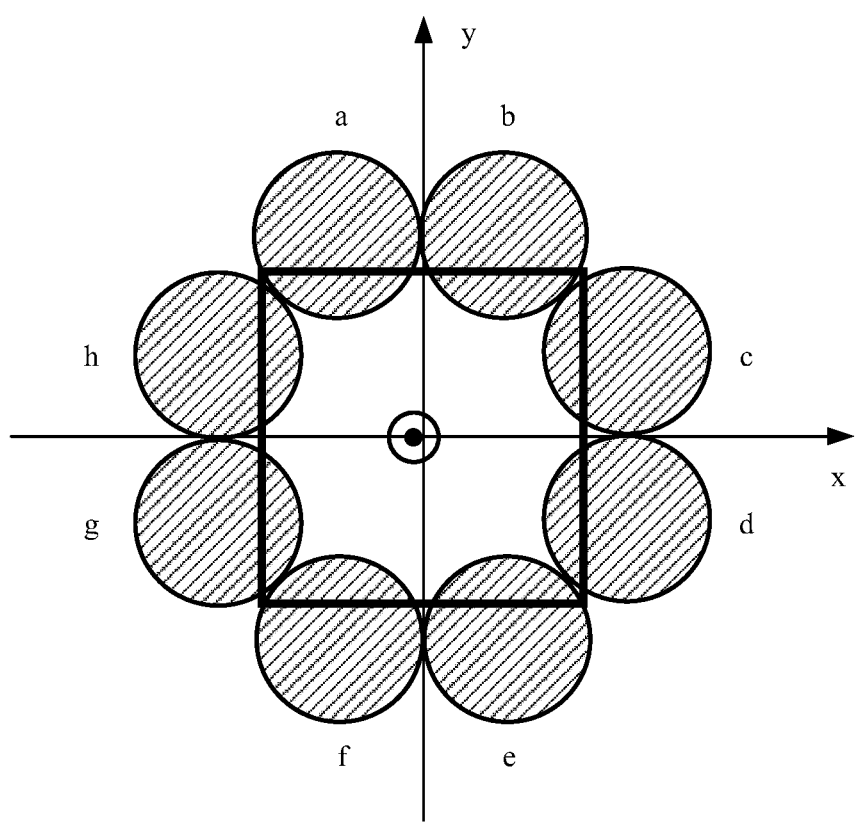
FIG. 6 is a schematic diagram of light intensity of reflected light measured by a photo detector in case a force in the positive direction of the z-axis is exerted on the tactile sensor according to an exemplary embodiment of this application.

FIG. 6 shows a schematic diagram of light intensity of reflected light measured by a photo detector 212 in case a force in the positive direction of the z-axis is exerted on the tactile sensor. in case a force along the z-axis is exerted on the tactile sensor, the reflector 213 at the top of the inner cavity of the elastomer support housing 22 is displaced along the z-axis. As a result, the light intensity of reflected light measured by the photo detector 212 decreases for each of the light source a to light source h.

In case force in a direction of translation along the z-axis is exerted on the tactile sensor, the light intensity of a first target light source measured by the photo detector 212 at moment i, and light intensity of the first target light source measured by the photo detector 212 at moment i+1 are acquired, where the first target light source may indicate at least one of the at least two light sources. The magnitude and direction of force exerted on the tactile sensor in a direction of translation along the z-axis in the touch event are acquired according to a third difference value and the first mapping relation; where the third difference value indicates a difference between the light intensity of the first target light source measured by the photo detector 212 at moment i and the light intensity of the first target light source measured by the photo detector at moment i+1.

For example, when the magnitude and direction of the force along the z-axis are to be measured, the light intensity of the reflected light may be measured by using at least one light source. For example, the light intensity of the reflected light may be measured by using only the light source c. In this case, it is required to measure the light intensity of the reflected light of the light source c before force in the positive direction of the z-axis is exerted on the tactile sensor, and measure the light intensity of the reflected light of the light source c after force in the positive direction of the z-axis is exerted on the tactile sensor in the positive direction of the z-axis. By calculating the difference in the light intensity of the light source c before and after force in the positive direction of the z-axis is exerted on the tactile sensor, the displacement produced by the reflector 213 at the top of the inner cavity of the elastomer support housing 22 along the z-axis is obtained, and then the magnitude of the force applied to the elastomer support housing 22 is obtained. For example, in case a force in a direction of translation along the z-axis is exerted on the tactile sensor, the correspondence between the displacement transz produced by the reflector of the tactile sensor along the z-axis and the light intensity measured by the photo detector 212 can be expressed as follows:

$$trans_z \propto \frac{\lambda_{c1} - \lambda_{c2}}{\lambda_{c1} + \lambda_{c2}}$$

$\lambda c1$ represents the light intensity of reflected light of the light source c measured by the photo detector at moment i; and $\lambda c2$ represents the light intensity of reflected light of the light source c measured by the photo detector at moment i+1.

Figure 7:
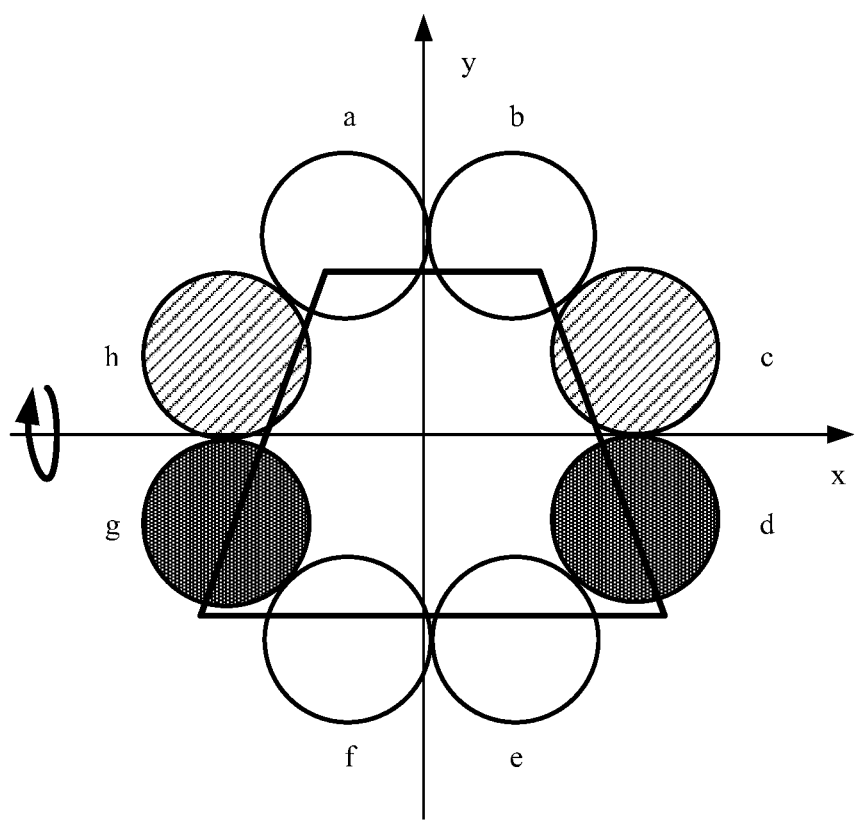
FIG. 7 is a schematic diagram of light intensity of reflected light measured by a photo detector in case a force of rotation about the x-axis is exerted on the tactile sensor according to an exemplary embodiment of this application.

FIG. 7 shows a schematic diagram of light intensity of reflected light measured by a photo detector in case a force of rotation about the x-axis is exerted on the tactile sensor.

In case force of rotation about the x-axis is exerted on the tactile sensor, that is, when torque around the x-axis is exerted on the tactile sensor, the reflector 213 at the top of the inner cavity of the elastomer support housing 22 rotates about the x-axis. As a result, the overall light intensity of the reflected light of the light source g and light source d measured by the photo detector 212 increases, while the overall light intensity of the reflected light of the light source h and light source c measured by the photo detector 212 decreases.

In case force in a direction of rotation about the x-axis is exerted on the tactile sensor, the first x-axis light source is turned on, and the light intensity of the first x-axis light source measured by the photo detector 212 is acquired when the first x-axis light source is in the "on" state; and the second x-axis light source is turned on, and the light intensity of the second x-axis light source measured by the photo detector 212 is acquired when the second x-axis light source is in the "on" state.

The magnitude and direction of force exerted on the tactile sensor in a direction of rotation about the x-axis in the touch event are acquired according to a fourth difference value and the second mapping relation.

The fourth difference value indicates a difference between the light intensity of the first x-axis light source measured by the photo detector 212 and the light intensity of the second x-axis light source measured by the photo detector 212. The first x-axis light source includes a first positive x-axis light source, and the second x-axis light source includes a second positive x-axis light source; or the first x-axis light source includes a first negative x-axis light source, and the second x-axis light source includes a second negative x-axis light source; or the first x-axis light source includes a first positive x-axis light source and a first negative x-axis light source, and the second x-axis light source includes a second positive x-axis light source and a second negative x-axis light source.

For example, in case a force in a direction of rotation about the x-axis is exerted on the tactile sensor, first, the light source g and the light source d are turned on, and the overall light intensity ($\lambda g + \lambda d$) of reflected light of the light source g and the light source d is measured using the photo detector 212. Then, the light source g and the light source d are turned off, the light source h and the light source g are turned on, and the overall light intensity ($\lambda h + \lambda c$) of reflected light of the light source h and the light source c is measured using the photo detector 212. By measuring the difference between the light intensity ($\lambda g + \lambda d$) and the light intensity ($\lambda h + \lambda c$), the rotational displacement or angle produced by the reflector 213 at the top of the inner cavity of the elastomer support housing 22 about the x-axis is obtained, and then the magnitude of the force applied to the elastomer support housing 22 is obtained. For example, in case a torque about the x-axis is exerted on the tactile sensor, the correspondence between the displacement revolx produced by the rotation of the reflector 213 of the tactile sensor about the x-axis and the light intensity measured by the photo detector 212 can be expressed as follows:

$$revol_x \propto \frac{(\lambda_g + \lambda_d) - (\lambda_h + \lambda_c)}{\lambda_c + \lambda_d + \lambda_h + \lambda_g}$$

$\lambda c$ represents the light intensity of reflected light of the light source c measured by the photo detector; $\lambda d$ represents the light intensity of reflected light of the light source d measured by the photo detector; $\lambda h$ represents the light intensity of reflected light of the light source h measured by the photo detector; and $\lambda g$ represents the light intensity of reflected light of the light source g measured by the photo detector.

It may be understood that, when the magnitude and direction of torque about the x-axis are to be measured, it is possible to conduct measurement by selecting at least two light sources on both sides of the x-axis, including but not limited to light source g and light source h, or light source d and light source c, which is not limited in the embodiments of this application.

Exemplarily, Table 2 (reference table of second mapping relation) shows a correspondence between the magnitude and direction of force exerted on the tactile sensor in a direction of rotation and changes in the light intensity measured by the photo detector. As shown in Table 2, in case a force in a direction of rotation is exerted on the tactile sensor, the light intensity of the reflected light of each of the light sources at a specific position is measured, or the light intensity of the reflected light of all the light sources is measured. For example, in case a force in a direction of rotation is exerted on the tactile sensor, the light intensity of the reflected light of each of the light sources at a specific position is measured to obtain the light intensity X1 and light intensity X2 corresponding to light source g and light source h, respectively. As can be seen from the correspondence between the rotational displacement transx produced by the reflector 213 of the tactile sensor along the x-axis and the light intensity measured by the photo detector 212, the reflector 213 at the top of the inner cavity of the elastomer support housing 22 produces a rotational displacement of Y1 along the x-axis; further, it is obtained that the force exerted on the tactile sensor in a direction of translation has a magnitude of aN, and is measured clockwise from the x-axis.

the photo detector 212 and the light intensity of the second y-axis light source measured by the photo detector 212. The first y-axis light source includes a first positive y-axis light source, and the second y-axis light source includes a second positive y-axis light source; or the first y-axis light source includes a first negative y-axis light source, and the second y-axis light source includes a second negative y-axis light source; or the first y-axis light source includes a first positive y-axis light source and a first negative y-axis light source, and the second y-axis light source includes a second positive y-axis light source and a second negative y-axis light source.

For example, first, the light source a and the light source f are turned on, and the overall light intensity ($\lambda a+\lambda f$) of reflected light of the light source a and the light source f is measured using the photo detector 212. Then, the light source a and the light source f are turned off, the light source e and the light source b are turned on, and the overall light intensity ($\lambda e+\lambda b$) of reflected light of the light source e and the light source b is measured using the photo detector 212. By measuring the difference between the light intensity ($\lambda a+\lambda f$) and the light intensity ($\lambda e+\lambda b$), the rotational displacement or angle produced by the reflector 213 at the top of the inner cavity of the elastomer support housing 22 about the y-axis is obtained, and then the magnitude of the force applied to the elastomer support housing is obtained. For example, in case a force in a direction of rotation about the y-axis is exerted on the tactile sensor, the correspondence between the displacement revoly produced by the rotation of

TABLE 2

Reference table of second mapping relation

| Position of light source to be tested | Measured light intensity/ Lux | Translational displacement/ mm | Magnitude of force/N | Direction of force | Magnitude of resultant force/N | Direction of resultant force |
|---|---|---|---|---|---|---|
| Light source g | X1 | Y1 | a | Clockwise from the x-axis | | |
| Light source h | X2 | | | | | |

Figure 8:
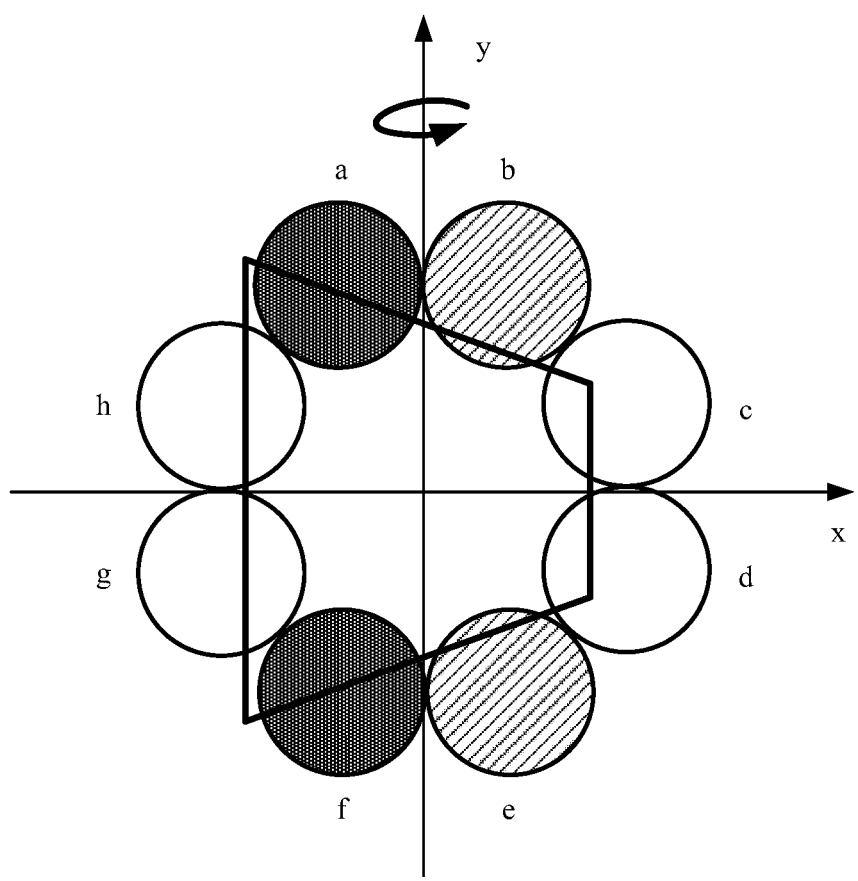
FIG. 8 is a schematic diagram of light intensity of reflected light measured by a photo detector in case a force of rotation about the y-axis is exerted on the tactile sensor according to an exemplary embodiment of this application.

Exemplarily, FIG. 8 shows a schematic diagram of light intensity of reflected light measured by a photo detector in case a force in a direction of rotation about the y-axis is exerted on the tactile sensor, in case a force of rotation about the y-axis is exerted on the tactile sensor, the reflector 213 at the top of the inner cavity of the elastomer support housing 22 rotates about the y-axis. As a result, the overall light intensity of the light source a and light source f measured by the photo detector 212 increases, while the overall light intensity of the light source b and light source e measured by the photo detector 212 decreases.

In case force in a direction of rotation about the y-axis is exerted on the tactile sensor, the first y-axis light source is turned on, and the light intensity of the first y-axis light source measured by the photo detector 212 is acquired when the first y-axis light source is in the "on" state; and the second y-axis light source is turned on, and the light intensity of the second y-axis light source measured by the photo detector 212 is acquired when the second y-axis light source is in the "on" state.

The magnitude and direction of force exerted on the tactile sensor in a direction of rotation about the x-axis in the touch event are acquired according to a fifth difference value and the second mapping relation.

The fifth difference value indicates a difference between the light intensity of the first y-axis light source measured by the reflector 213 of the tactile sensor about the y-axis and the light intensity measured by the photo detector 212 can be expressed as follows:

$$revol_y \propto \frac{(\lambda_a + \lambda_f) - (\lambda_e + \lambda_b)}{\lambda_a + \lambda_b + \lambda_e + \lambda_f}$$

$\lambda a$ represents the light intensity of reflected light of the light source a measured by the photo detector; $\lambda b$ represents the light intensity of reflected light of the light source b measured by the photo detector; $\lambda e$ represents the light intensity of reflected light of the light source e measured by the photo detector; and $\lambda f$ represents the light intensity of reflected light of the light source f measured by the photo detector.

It may be understood that, when the magnitude and direction of the torque about the y-axis are to be measured, it is possible to conduct measurement by selecting at least two light sources on both sides of the y-axis, including but not limited to light source a and light source b, or light source a and light source e, or light source b and light source f, or light source f and light source e, which is not limited in the embodiments of this application.

Figure 9:
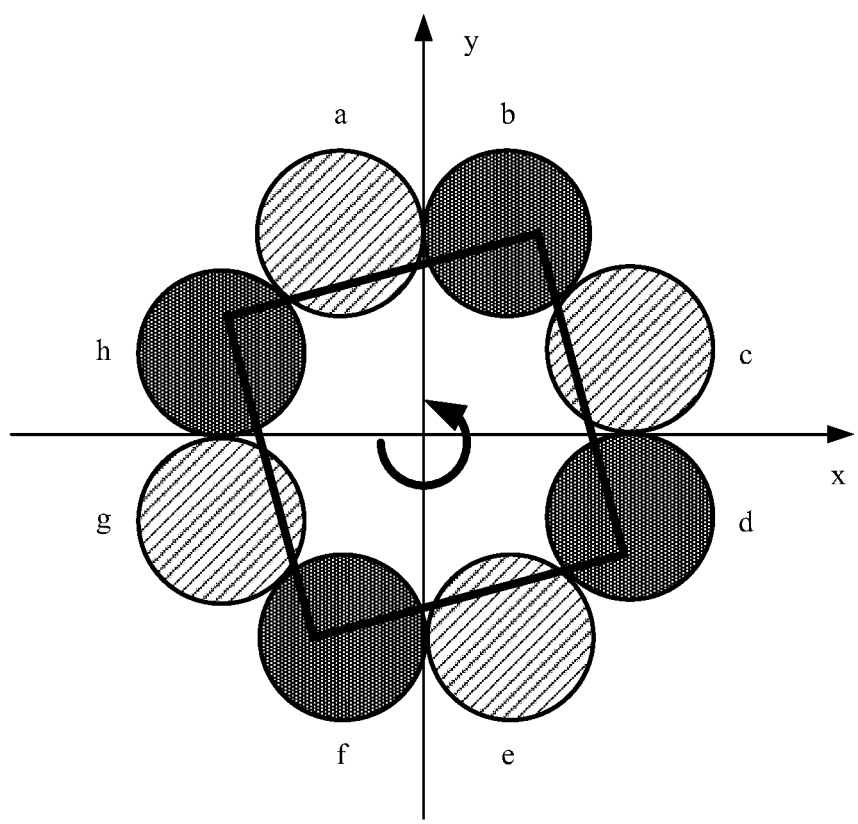
FIG. 9 is a schematic diagram of light intensity of reflected light measured by a photo detector in case a force of rotation about the z-axis is exerted on the tactile sensor according to an exemplary embodiment of this application.

Exemplarily, FIG. 9 shows a schematic diagram of light intensity of reflected light measured by a photo detector in case a force in a direction of rotation about the z-axis is exerted on the tactile sensor, in case a force along the z-axis is exerted on the tactile sensor, the reflector 213 at the top of the inner cavity of the elastomer support housing 22 rotates about the z-axis. As a result, the light intensity of the reflected light measured by the photo detector 212 decreases for each of the light source a, light source c, light source e and light source g, while the light intensity of the reflected light measured by the photo detector 212 increases for each of the light source b, light source d, light source f and light source h.

In case force in a direction of rotation about the z-axis is exerted on the tactile sensor, the second target light source is turned on, and the light intensity of the second target light source measured by the photo detector is acquired when the second target light source is in the "on" state; and the third target light source is turned on, and the light intensity of the third target light source measured by the photo detector is acquired when the third target light source is in the "on" state; where the second target light source is any one of the at least two light sources, and the third target light source is a light source of the at least two light sources other than the second target light source.

The magnitude and direction of force exerted on the tactile sensor in a direction of rotation about the z-axis in the touch event are acquired according to a sixth difference value and the second mapping relation.

The sixth difference value may indicate a difference between the light intensity of the second target light source measured by the photo detector 212 and the light intensity of the third target light source measured by the photo detector 212.

It may be understood that, when the magnitude and direction of the torque about the z-axis are to be measured, it is possible to conduct measurement by selecting all the light sources or at least two light sources, including but not limited to light source a and light source b, or light source a and light source d, or light source a and light source f, or light source a and light source h, or light source c and light source d, which is not limited in the embodiments of this application.

For example, first, the light source b, light source d, light source f and light source h are turned on, and the overall light intensity ($\lambda b+\lambda d+\lambda h+\lambda f$) of reflected light of the light source b, light source d, light source f and light source h is measured using the photo detector 212. Then, the light source b, light source d, light source f and light source h are turned off, the light source a, light source c, light source e and the light source g are turned on, and the overall light intensity ($\lambda a+\lambda c+\lambda e+\lambda g$) of reflected light of the light source a, light source c, light source e and the light source g is measured using the photo detector 212. By measuring the difference between the light intensity ($\lambda b+\lambda d+\lambda h+\lambda f$) and the light intensity ($\lambda a+\lambda c+\lambda e+\lambda g$), the rotational displacement or angle produced by the reflector 213 at the top of the inner cavity of the elastomer support housing 22 about the z-axis is obtained, and then the magnitude of the force applied to the elastomer support housing 22 is obtained. For example, in case a force in a direction of rotation about the z-axis is exerted on the tactile sensor, the correspondence between the displacement revolz produced by the rotation of the reflector 213 of the tactile sensor about the z-axis and the light intensity measured by the photo detector 212 can be expressed as follows:

$$revol_z \propto \frac{(\lambda_a + \lambda_c + \lambda_e + \lambda_g) - (\lambda_b + \lambda_d + \lambda_h + \lambda_f)}{\lambda_a + \lambda_b + \lambda_c + \lambda_d + \lambda_e + \lambda_f + \lambda_g + \lambda_h}$$

To sum up, with the tactile sensor in the embodiment, the light intensity of the reflected light of different light sources is measured using the photo detector, so as to measure the magnitude and direction of force in a direction of translation and direction of rotation. A person skilled in the art may select an appropriate number of light sources according to the actual measurement situation, and select appropriate light sources for reflected light measurement, so as to make the measurement results of the tactile sensor more accurate.

Figure 10:
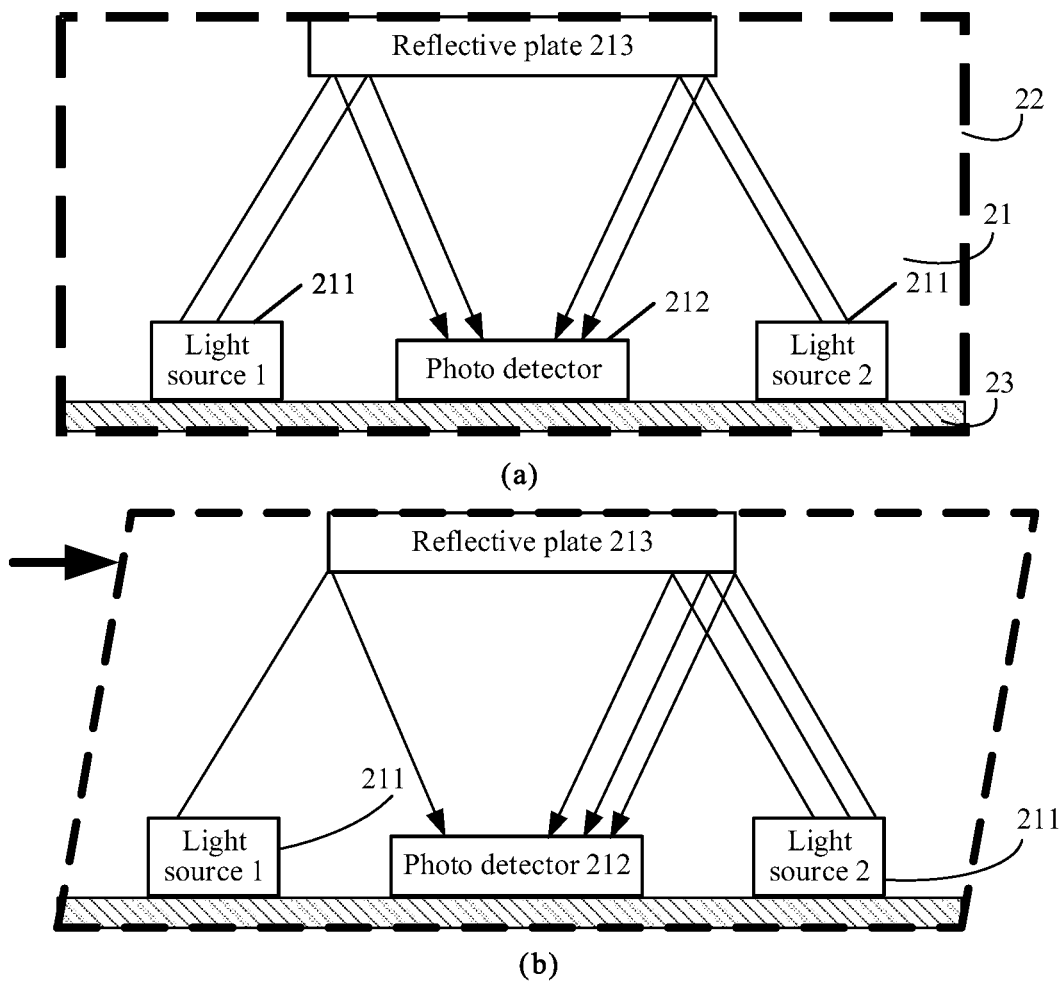
FIG. 10 is a schematic structural diagram of a tactile sensor according to an exemplary embodiment of this application.

FIG. 10($a$) shows a schematic structural diagram of a profile of a tactile sensor according to an exemplary embodiment of this application. The tactile sensor includes: a sensing unit 21, an elastomer support housing 22 and a base 23.

The sensing unit 21 is disposed in an inner cavity enclosed by the elastomer support housing 22 and the base 23.

The sensing unit 21 includes at least two light sources 211, a photo detector 212 and a reflector 213, where the photo detector 212 is disposed on base 23, the at least two light sources 211 are disposed around the periphery of the photo detector 212 on the base 23, and the reflector 21 is disposed at the top of an inner cavity of the elastomer support housing 22. For example, FIG. 10($a$) shows at least two light sources 211 including a light source 1 and a light source 2.

Exemplarily, the light source 211 may be at least one of a visible-light lamp or infrared lamp, which is not limited in the embodiments of this application. The reflector 213 is configured to reflect the light emitted by the light source 211 to the photo detector 212 through the reflector 213, and there is a sufficient color contrast between the reflector 213 and the top of the inner cavity of the elastomer support housing 22. The contrast refers to the color difference between the reflector 213 and the top of the inner cavity of the elastomer support housing 22 under the light source 211. The photo detector 212 is configured to receive the light intensity of the light emitted by the light source 211 and convert an optical signal into an electrical signal.

In a possible implementation, the base 23 may include an x-axis and a y-axis, where the x-axis and y-axis intersect each other at an origin, the photo detector 212 may be disposed at the origin, and at least two light sources 211 may include a positive x-axis light source and a negative x-axis light source which are located on the positive half axis and negative half axis of the x-axis, respectively.

At least two light sources 211 may also include a positive y-axis light source and a negative y-axis light source which are located on the positive half axis and negative half axis of the y-axis, respectively.

In a possible implementation, the positive x-axis light source and negative x-axis light source are centrally symmetrical with the origin as a center of symmetry; and/or the positive y-axis light source and negative y-axis light source are centrally symmetrical with the origin as a center of symmetry.

In a possible implementation, the positive x-axis light source may include n1light sources, and at least two of the n1 light sources are located on both sides of the positive half axis of the x-axis, where n1 is an integer greater than 2; and/or the negative x-axis light source may include n2 light sources, and at least two of the n2 light sources are located on both sides of the negative half axis of the x-axis, where n2 is an integer greater than 2. For example, n1 light sources are arranged in a straight line perpendicular to the positive half axis of the x-axis, or n1 light sources are arranged in a sector so that the light sources in the n1 light sources are at the same distance from the origin. n2 light sources are arranged in a straight line perpendicular to the negative half axis of the x-axis, or n2 light sources are arranged in a sector so that the light sources in the n2 light sources are at the same distance from the origin.

The positive y-axis light source may include n3 light sources, and at least two of the n3 light sources are located on both sides of the positive half axis of the y-axis, where n3 is an integer greater than 2; and/or the negative y-axis light source includes n4 light sources, and at least two of the n4 light sources are located on both sides of the negative half axis of the y-axis, where n4 is an integer greater than 2.

For example, n3 light sources are arranged in a straight line perpendicular to the positive half axis of the y-axis, or n3 light sources are arranged in a sector so that the light sources in the n3 light sources are at the same distance from the origin. n4 light sources are arranged in a straight line perpendicular to the negative half axis of the y-axis, or n4 light sources are arranged in a sector so that the light sources in the n4 light sources are at the same distance from the origin.

In a possible implementation, the sensing unit 21 includes eight light sources 211. The eight light sources 211 include a light source a, a light source b, a light source c, a light source d, a light source e, a light source f, a light source g and a light source h, respectively, and the eight light sources 211 are disposed around the periphery of the photo detector 212 on the base 23. The positive x-axis light source, the negative x-axis light source, the positive y-axis light source and the negative y-axis light source each include two light sources; where the light source a is a first positive y-axis light source, and the light source b is a second positive y-axis light source; the light source c is a first positive x-axis light source, and the light source d is a second positive x-axis light source; the light source e is a first negative y-axis light source, and the light source f is a second negative y-axis light source; and the light source g is a first negative x-axis light source, and the light source h is a second negative x-axis light source.

In a possible implementation, the tactile sensor includes a photo detector 212 and a plurality of light sources 211. The plurality of light sources 211 include at least two light sources 211 disposed on the positive half axis and the negative half axis of a coordinate axis; and/or the plurality of light sources 211 include at least two light sources 211 disposed on both sides of the coordinate axis.

Exemplarily, the upper surface of the elastomer support housing 22 is offset when force is applied to the elastomer support housing 22, thereby driving the reflector 213 at the top of the inner cavity of the elastomer support housing 22 to be offset, which further results in a change in the light intensity of reflected light received by the photo detector 212. The on/off of the light sources 211 are controlled in turn, and the photo detector 212 measures the light intensity of the reflected light of each of the light sources 211. By calculating the changes in the light intensity of the reflected light of each of the light sources 211, the displacement of the reflector 213 at the top of the inner cavity of the elastomer support housing 22 is calculated, and then the magnitude and direction of the force exerted on the tactile sensor are acquired.

As shown in FIG. 10(b), when force in a direction of translation is applied to the elastomer support housing 22, only the light source 1 is turned on, and the light intensity of reflected light of the light source 1 is measured using the photo detector 212; and upon the measurement of the light intensity of the reflected light of the light source 1, the light source 1 is turned off, and the light source 2 is turned on. As shown in FIG. 10(b), the light intensity of the reflected light of the light source 2 is measured using the photo detector 212. By measuring the difference value between the light intensity of the reflected light of the light source 1 and the light intensity of the reflected light of the light source 2, the displacement produced by the reflector 213 at the top of the inner cavity of the elastomer support housing 22 is calculated, and then the magnitude and direction of the force applied to the elastomer support housing 22 are obtained.

In a possible implementation, there is no intersection between a projection area of the reflector 213 on the base 23 and the disposing position of the light source 211. Exemplarily, the projection area of the reflector 213 on the base 23 does not coincide with the light source 211, that is, the light source is located outside the projection area of the reflector 213 on the base 23, so that the photo detector 212 has improved sensitivity and accuracy in measuring changes in light intensity of the reflected light when the reflector 213 at the top of the inner cavity of the elastomer support housing 22 is displaced. For example, FIG. 10(b) shows at least two light sources 211 including the light source 1 and light source 2.

In a possible implementation, one or a plurality of reflectors 213 are disposed. In case one reflector 213 is disposed, the reflector 213 is in a shape of a regular polygon. The projection area of the regular polygon on the base 23 does not coincide with the light source 211. In case a plurality of reflectors 213 are disposed, the plurality of reflectors 213 are disposed according to a layout of a regular polygon, or the plurality the reflectors 213 are disposed according to a layout of a circle.

For example, in case a plurality of reflectors 213 are disposed, the plurality of reflectors 213 are disposed according to a layout of a regular polygon, and the projection area of the plurality of reflectors 213 disposed according to a layout of a regular polygon on the base 23 is located between the photo detector 212 and the light source 211; or the plurality of reflectors 213 are disposed according to a layout of a circle, and the projection area of the plurality of reflectors 213 disposed according to a layout of a circle on the base 23 is located between the photo detector 212 and the light source 211.

In a possible implementation, the shape of the reflector 213 may specifically be, but not limited to, at least one of a rectangle, an oval, or a triangle, which is not limited in the embodiments of this application.

Figure 11:
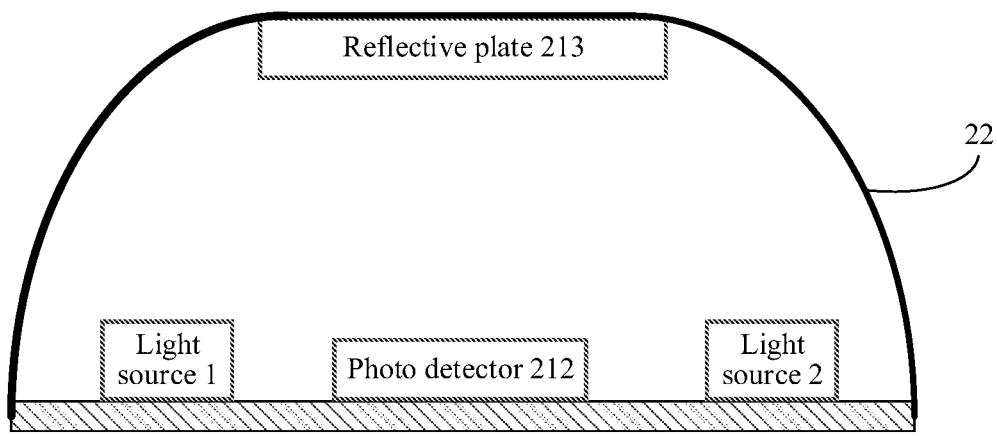
FIG. 11 is a schematic structural diagram of a tactile sensor according to an exemplary embodiment of this application.

In case the sensing unit includes at least two light sources (e.g., light source 1 and light source 2), a photo detector 212 and a reflector 213, as shown in FIG. 11, in a possible implementation, the elastomer support housing 22 is of an integral structure. The elastomer support housing 22 may be made of a silicone material as a whole in case the elastomer support housing 22 is of an integral structure. In case the elastomer support housing 22 is of an integral structure, and the shape of the elastomer support housing 22 may specifically be, but not limited to, at least one of a rectangle, bowl, hemisphere or ellipsoid, which is not limited in the embodiments of this application.

Figure 12:
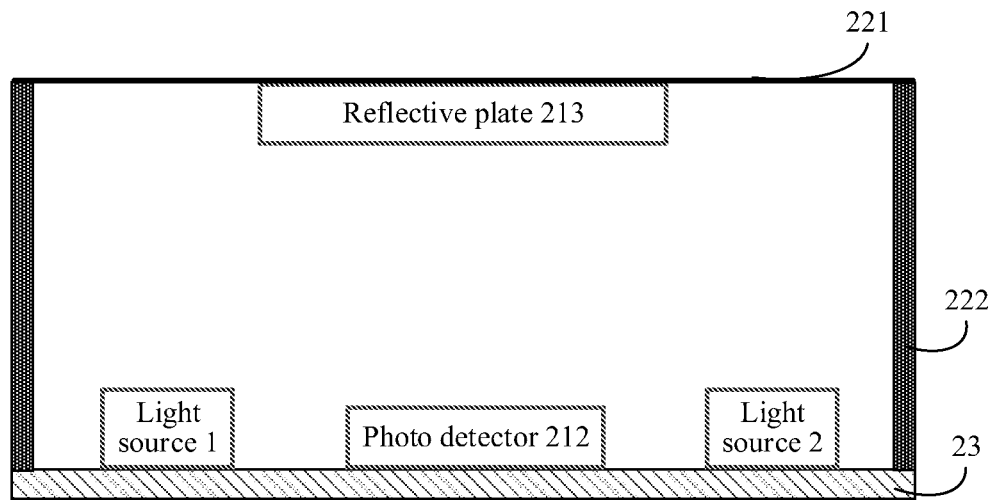
FIG. 12 is a schematic structural diagram of a tactile sensor according to an exemplary embodiment of this application.

In a possible implementation, in case the sensing unit includes at least two light sources (e.g., light source 1 and light source 2), a photo detector 212 and a reflector 213, as shown in FIG. 12, the elastomer support housing is of an assembled structure and the elastomer support housing 22 includes a rigid plate 221 and a deformable support 222, where the rigid plate 221 is connected to the base 23 through the deformable support 222, and the reflector 213 is fixed to the lower surface of the rigid plate 221. The deformable support 222 includes at least one of a spring, a rubber material and a foam material, which is not limited in the embodiments of this application.

In a possible implementation, a photo detector 212 may be disposed in a central area of the base 23, at least two light sources 211 are disposed around the periphery of the photo detector 212 on the base 23, and the reflector 213 is disposed at the top of an inner cavity of the elastomer support housing 22.

Figure 13:
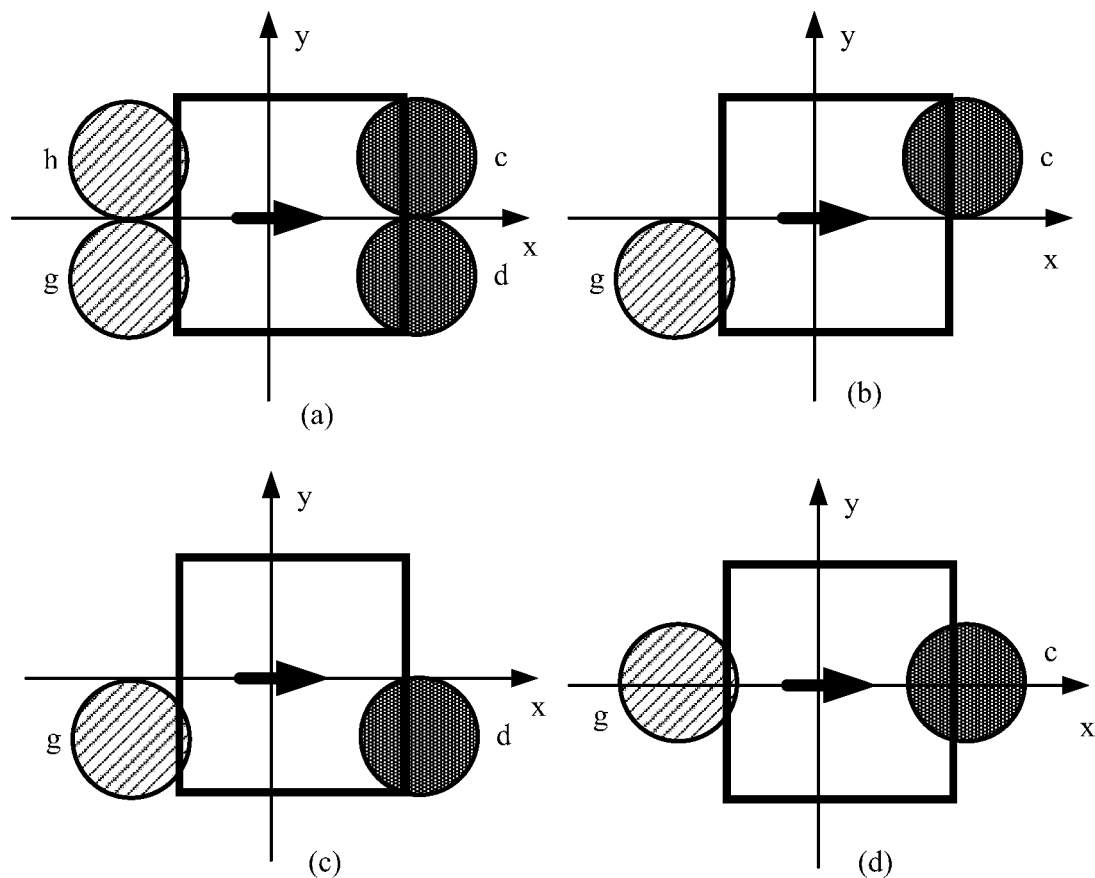
FIG. 13 is a schematic diagram of light intensity of reflected light measured by a photo detector in case a force in the positive direction of the x-axis is exerted on the tactile sensor according to an exemplary embodiment of this application.

In a possible implementation, in case a force in a direction of translation along the x-axis is applied to the elastomer support housing 22, is shown in FIG. 13(a), the overall light intensity ($\lambda c+\lambda d$) of reflected light of the light source c and light source d is measured using the photo detector 212. Then, the overall light intensity ($\lambda h+\lambda g$) of reflected light of the light source h and light source g is measured using the photo detector 212. By measuring the difference between the light intensity ($\lambda c+\lambda d$) and the light intensity ($\lambda h+\lambda g$), the displacement produced by the reflector 213 at the top of the inner cavity of the elastomer support housing 22 along the x-axis is obtained, and then the magnitude and direction of the force applied to the elastomer support housing 22 are obtained. As shown in FIG. 13(b), the light intensity $\lambda c$ of reflected light of the light source c is measured using the photo detector 212. Then, the light intensity 4 of reflected light of the light source g is measured using the photo detector 212. By measuring the difference between the light intensity ($\lambda c$) and the light intensity ($\lambda g$), the displacement produced by the reflector 213 at the top of the inner cavity of the elastomer support housing 22 along the x-axis is obtained, and then the magnitude and direction of the force applied to the elastomer support housing 22 are obtained. As shown in FIG. 13(c), the light intensity $\lambda d$ of reflected light of the light source d is measured using the photo detector 212. Then, the overall light intensity $\lambda g$ of reflected light of the light source g is measured using the photo detector 212. By measuring the difference between the light intensity ($\lambda d$) and the light intensity ($\lambda g$), the displacement produced by the reflector 213 at the top of the inner cavity of the elastomer support housing 22 along the x-axis is obtained, and then the magnitude and direction of the force applied to the elastomer support housing 22 are obtained. As shown in FIG. 13(d), the light source c and light source g are disposed on the x-axis, and the light intensity $\lambda c$ of reflected light of the light source c is measured using the photo detector 212. Then, the light intensity $\lambda g$ of reflected light of the light source g is measured using the photo detector 212. By measuring the difference between the light intensity ($\lambda c$) and the light intensity ($\lambda g$), the displacement produced by the reflector 213 at the top of the inner cavity of the elastomer support housing 22 along the x-axis is obtained, and then the magnitude and direction of the force applied to the elastomer support housing 22 are obtained.

Figure 14:
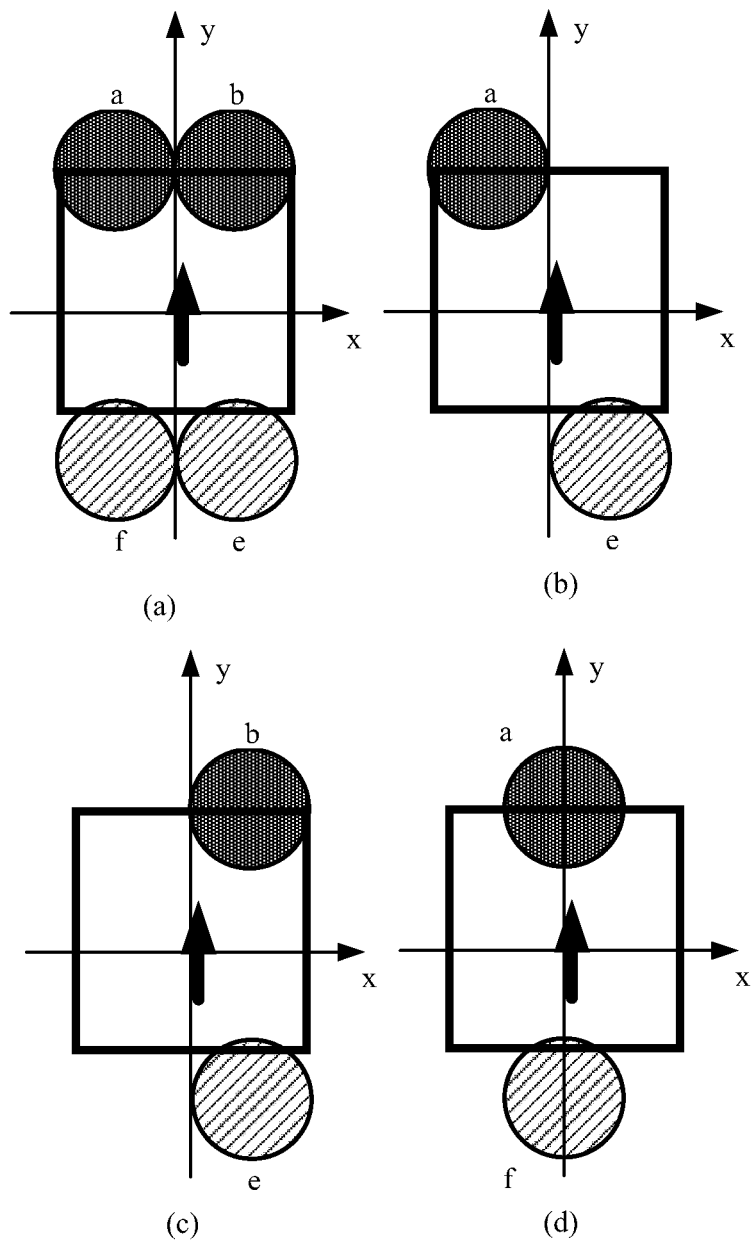
FIG. 14 is a schematic diagram of light intensity of reflected light measured by a photo detector in case a force in the positive direction of the y-axis is exerted on the tactile sensor according to an exemplary embodiment of this application.

In a possible implementation, in case a force in a direction of translation along the y-axis is applied to the elastomer support housing 22, as shown in FIG. 14(a), the overall light intensity ($\lambda a+\lambda b$) of reflected light of the light source a and light source b is measured using the photo detector 212. Then, the overall light intensity ($\lambda e+\lambda f$) of reflected light of the light source e and light source f is measured using the photo detector 212. By measuring the difference between the light intensity ($\lambda a+\lambda b$) and the light intensity ($\lambda e+\lambda f$), the displacement produced by the reflector 213 at the top of the inner cavity of the elastomer support housing 22 along the y-axis is obtained, and then the magnitude and direction of the force applied to the elastomer support housing 22 is obtained. As shown in FIG. 14(b), the light intensity $\lambda a$ of reflected light of the light source a is measured using the photo detector 212. Then, the light intensity $\lambda e$ of reflected light of the light source e is measured using the photo detector 212. By measuring the difference between the light intensity ($\lambda$) and the light intensity ($\lambda e$), the displacement produced by the reflector 213 at the top of the inner cavity of the elastomer support housing 22 along the y-axis is obtained, and then the magnitude and direction of the force applied to the elastomer support housing 22 are obtained. As shown in FIG. 14(c), the overall light intensity a of reflected light of the light source b is measured using the photo detector 212. Then, the light intensity $\lambda e$ of reflected light of the light source e is measured using the photo detector 212. By measuring the difference between the light intensity ($\lambda b$) and the light intensity ($\lambda e$), the displacement produced by the reflector 213 at the top of the inner cavity of the elastomer support housing 22 along the y-axis is obtained, and then the magnitude and direction of the force applied to the elastomer support housing 22 are obtained. As shown in FIG. 14(d), the light source a and light source f are disposed on the x-axis, and the light intensity Aa of reflected light of the light source a is measured using the photo detector 212. Then, the light intensity $\lambda f$ of reflected light of the light source f is measured using the photo detector 212. By measuring the difference between the light intensity ($\lambda a$) and the light intensity ($\lambda f$), the displacement produced by the reflector 213 at the top of the inner cavity of the elastomer support housing 22 along the y-axis is obtained, and then the magnitude and direction of the force applied to the elastomer support housing 22 are obtained.

Figure 15:
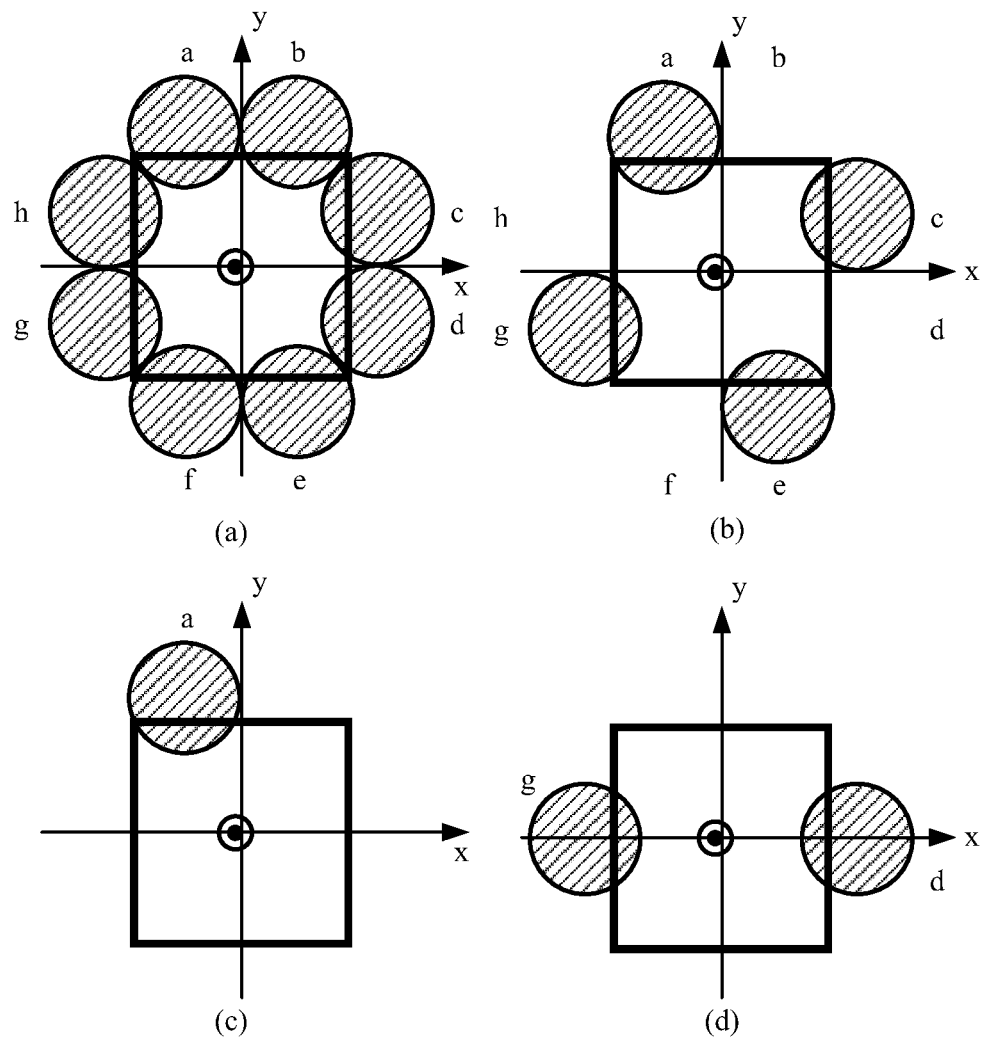
FIG. 15 is a schematic diagram of light intensity of reflected light measured by a photo detector in case a force in the positive direction of the z-axis is exerted on the tactile sensor according to an exemplary embodiment of this application.

In a possible implementation, in case a force in a direction of translation along the z-axis is applied to the elastomer support housing 22, as shown in FIG. 15(a), the overall light intensity of reflected light of all the light sources is measured at moment i using the photo detector 212. Then, the overall light intensity of reflected light of all the light sources is measured at moment i+1 using the photo detector 212. By measuring the difference in the overall light intensity of all the light sources measured at the two moments, the displacement produced by the reflector 213 at the top of the inner cavity of the elastomer support housing 22 along the z-axis is obtained, and then the magnitude and direction of the force applied to the elastomer support housing 22 are obtained. As shown in FIG. 15(b), the overall light intensity ($\lambda a1+\lambda c1+\lambda e1+\lambda g1$) of reflected light of some of the light sources is measured at moment i using the photo detector 212. Then, the overall light intensity ($\lambda a2+\lambda c2+\lambda e2+\lambda g2$) of reflected light of some of the light sources is measured at moment i+1 using the photo detector 212. By measuring the difference in the overall light intensity of the light sources measured at the two moments, the displacement produced by the reflector 213 at the top of the inner cavity of the elastomer support housing 22 along the z-axis is obtained, and then the magnitude and direction of the force applied to the elastomer support housing 22 are obtained. As shown in FIG. 15(c), the overall light intensity $\lambda a1$ of reflected light of a single light source is measured at moment i using the photo detector 212. Then, the overall light intensity $\lambda a2$ of reflected light of a single light source is measured at moment i+1 using the photo detector 212. By measuring the difference in the overall light intensity of the light sources measured at the two moments, the displacement produced by the reflector 213 at the top of the inner cavity of the elastomer support housing 22 along the z-axis is obtained, and then the magnitude and direction of the force applied to the elastomer support housing 22 are obtained. As shown in FIG. 15(d), the light source is disposed on the x-axis, and the overall light intensity ($\lambda g1+\lambda d1$) of reflected light of two light sources is measured at moment i using the photo detector 212. Then, the overall light intensity ($\lambda g2+\lambda d2$) of reflected light of two light sources is measured at moment i+1 using the photo detector 212. By measuring the difference in the overall light intensity of the light sources measured at the two moments, the displacement produced by the reflector 213 at the top of the inner cavity of the elastomer support housing 22 along the z-axis is obtained, and then the magnitude and direction of the force applied to the elastomer support housing 22 are obtained.

It may be understood that, the light sources selected for the above measurement of the magnitude and direction of the force applied to the elastomer support housing 22 in a direction of translation are not limited thereto, and measurement can be conducted with a suitable location and an appropriate number of light sources according to the actual demand, which is not limited in the embodiments of this application.

In case force in a direction of translation is exerted on the tactile sensor, this embodiment provides a variety of possible solutions for measuring the light intensity of the reflected light of the light sources corresponding to the positive half axis and negative half axis in a direction of translation. By calculating the changes in the light intensity of the reflected light of the light sources corresponding to the positive half axis and negative half axis in a direction of translation, the magnitude and direction of the force exerted on the tactile sensor in a direction of translation are sensed.

Figure 16:
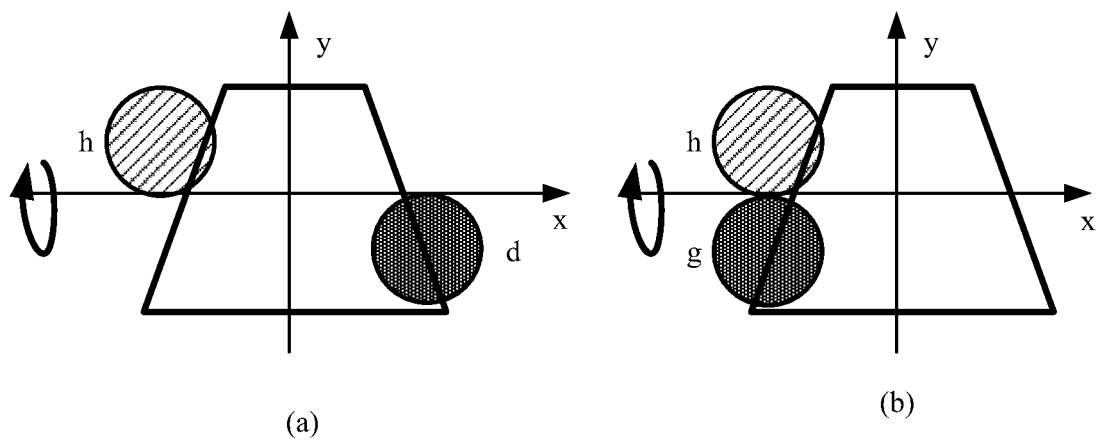
FIG. 16 is a schematic diagram of light intensity of reflected light measured by a photo detector in case a force of rotation about the x-axis is exerted on the tactile sensor according to an exemplary embodiment of this application.

In a possible implementation, in case a force in a direction of rotation about the x-axis is applied to the elastomer support housing 22, as shown in FIG. 16(a), the overall light intensity ($\lambda d$) of reflected light of the light source light source d is measured using the photo detector 212. Then, the overall light intensity $\lambda h$ of reflected light of the light source h is measured using the photo detector. By measuring the difference between the light intensity ($\lambda d$) and the light intensity ($\lambda h$), the rotational displacement or angle produced by the reflector at the top of the inner cavity of the elastomer support housing 22 about the x-axis is obtained, and then the magnitude of the force applied to the elastomer support housing 22 is obtained. As shown in FIG. 16(b), the overall light intensity ($\lambda g$) of reflected light of the light source g is measured using the photo detector 212. Then, the overall light intensity $\lambda h$ of reflected light of the light source h is measured using the photo detector. By measuring the difference between the light intensity ($\lambda g$) and the light intensity ($\lambda h$), the rotational displacement or angle produced by the reflector 213 at the top of the inner cavity of the elastomer support housing 22 about the x-axis is obtained, and then the magnitude of the force applied to the elastomer support housing is obtained.

Figure 17:
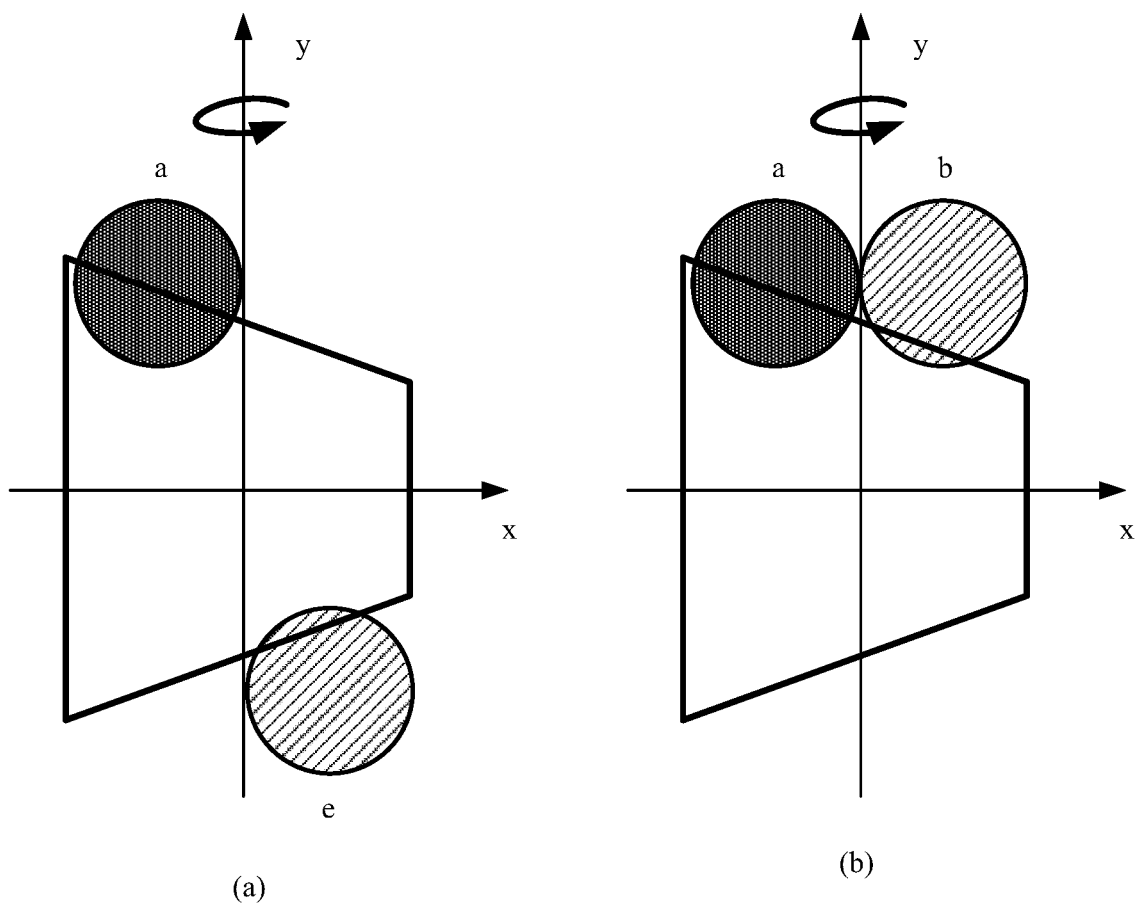
FIG. 17 is a schematic diagram of light intensity of reflected light measured by a photo detector in case a force of rotation about the y-axis is exerted on the tactile sensor according to an exemplary embodiment of this application.

In a possible implementation, in case a force in a direction of rotation about the y-axis is applied to the elastomer support housing 22, the overall light intensity ($\lambda a$) of reflected light of the light source a is measured using the photo detector 212, as shown in FIG. 17(a). Then, the overall light intensity $\lambda e$ of reflected light of the light source e is measured using the photo detector. By measuring the difference between the light intensity ($\lambda a$) and the light intensity ($\lambda e$), the rotational displacement or angle produced by the reflector 213 at the top of the inner cavity of the elastomer support housing 22 about the y-axis is obtained, and then the magnitude of the force applied to the elastomer support housing 213 is obtained. As shown in FIG. 17(b), the overall light intensity $\lambda a$ of reflected light of the light source a is measured using the photo detector 212. Then, the overall light intensity $\lambda b$ of reflected light of the light source b is measured using the photo detector. By measuring the difference between the light intensity ($\lambda a$) and the light intensity ($\lambda b$), the rotational displacement or angle produced by the reflector 213 at the top of the inner cavity of the elastomer support housing 22 about the y-axis is obtained, and then the magnitude of the force applied to the elastomer support housing 22 is obtained.

Figure 18:
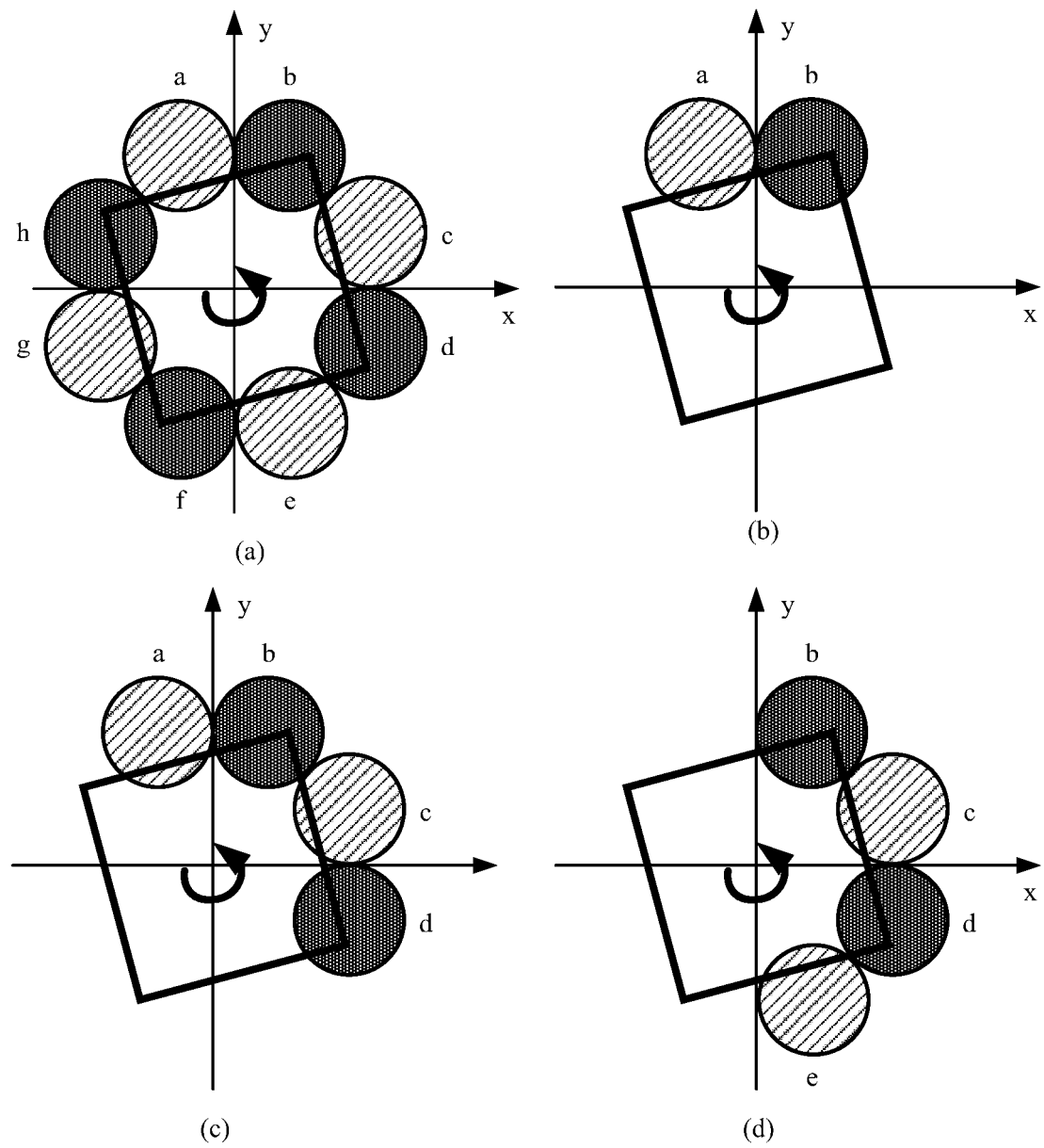
FIG. 18 is a schematic diagram of light intensity of reflected light measured by a photo detector in case a force of rotation about the z-axis is exerted on the tactile sensor according to an exemplary embodiment of this application.

In a possible implementation, in case a force in a direction of rotation along the z-axis is applied to the elastomer support housing 22, as shown in FIG. 18(a), the overall light intensity ($\lambda a+\lambda c+\lambda e+\lambda g$) of the light source a, light source c, light source e and light source g is measured using the photo detector 212. Then, the overall light intensity ($\lambda b+\lambda d+\lambda f+\lambda h$) of reflected light of the light source b, light source d, light source f and light source h is measured using the photo detector. By measuring the difference between the light intensity ($\lambda a+\lambda c+\lambda e+\lambda g$) and the light intensity ($\lambda b+\lambda d+\lambda f+\lambda h$), the rotational displacement or angle produced by the reflector at the top of the inner cavity of the elastomer support housing 22 about the z-axis is obtained, and then the magnitude of the force applied to the elastomer support housing 22 is obtained. As shown in FIG. 18(b), the overall light intensity $\lambda a$ of reflected light of the light source a is measured using the photo detector 212. Then, the overall light intensity $\lambda b$ of reflected light of the light source b is measured using the photo detector. By measuring the difference between the light intensity ($\lambda a$) and the light intensity ($\lambda b$), the rotational displacement or angle produced by the reflector 213 at the top of the inner cavity of the elastomer support housing 22 about the z-axis is obtained, and then the magnitude of the force applied to the elastomer support housing 22 is obtained. As shown in FIG. 18(c), the overall light intensity ($\lambda a+\lambda c$) of reflected light of the light source a and light source c is measured using the photo detector 212. Then, the overall light intensity ($\lambda b+\lambda d$) of reflected light of the light source b and light source d is measured using the photo detector 212. By measuring the difference between the light intensity ($\lambda a+\lambda c$) and the light intensity ($\lambda b+\lambda d$), the rotational displacement or angle produced by the reflector 213 at the top of the inner cavity of the elastomer support housing 22 about the z-axis is obtained, and then the magnitude of the force applied to the elastomer support housing 22 is obtained. As shown in FIG. 18(d), the overall light intensity ($\lambda c+\lambda e$) of reflected light of the light source c and light source e is measured using the photo detector 212. Then, the overall light intensity ($\lambda b+\lambda d$) of reflected light of the light source b and light source d is measured using the photo detector. By measuring the difference between the light intensity ($\lambda c+\lambda e$) and the light intensity ($\lambda b+\lambda d$), the rotational displacement or angle produced by the reflector 213 at the top of the inner cavity of the elastomer support housing 22 about the z-axis is obtained, and then the magnitude of the force applied to the elastomer support housing 22 is obtained.

It may be understood that, the light sources selected for the above measurement of the magnitude and direction of the force applied to the elastomer support housing 22 in a direction of rotation are not limited thereto, and measurement can be conducted with a suitable location and an appropriate number of light sources according to the actual demand, which is not limited in the embodiments of this application.

In case force in a direction of rotation is exerted on the tactile sensor, this embodiment provides a variety of possible solutions for measuring the light intensity of the reflected light of the light sources on both sides of a rotation axis. By calculating the changes in the light intensity of the reflected light of the light sources on both sides of the rotation axis, the magnitude and direction of the force exerted on the tactile sensor in a direction of rotation are sensed.

To sum up, by adopting the combination of a plurality of light sources and one photo detector for the tactile sensor in this embodiment, the number of photo detectors for use is reduced, so that the volume of the tactile sensor is reduced. In the meanwhile, with the reduction in the number of photo detectors, readout circuits special for the photo detector are reduced accordingly, which makes the tactile sensor simpler in structure and faster in measurement speed.

To sum up, the tactile sensor in the embodiment measures the light intensity of the reflected light of each of the light sources through a plurality of light sources and a photo detector, thus sensing the magnitude and direction of force in six degrees of freedom, such as a direction of translation and a direction of rotation.

Based on the description of the structure of the tactile sensor in the above embodiment, the preparation method for the tactile sensor is described below.

Figure 19:
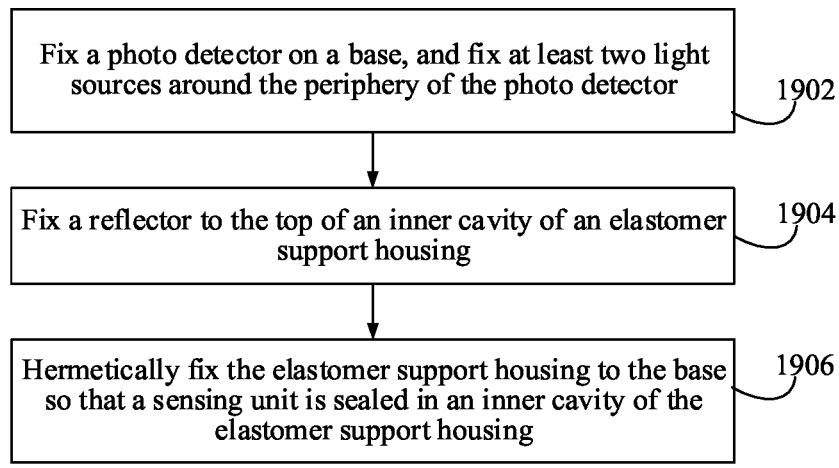
FIG. 19 is a flowchart of a preparation method for a tactile sensor according to an exemplary embodiment of this application.

FIG. 19 shows a flowchart of a preparation method for a tactile sensor according to an exemplary embodiment of this application. The method is applied to the preparation of the tactile sensor, and an executive body of the method can be industrial flowline equipment.

Step 1902: Fix a photo detector on a base, and fix at least two light sources around the periphery of the photo detector.

Exemplarily, the base 23 is a printed circuit board (PCB), where the photo detector 212 may be fixed to the base 23 by welding, and at least two light sources 23 may also be fixed to the periphery of the photo detector 212 by welding.

Exemplarily, the photo detector 212 may be fixed to the central area of the base 23 by glue, and at least two light sources 211 may also be fixed to the periphery of the photo detector 212 by glue.

It may be understood that, the foregoing method of fixing the photo detector 212 and at least two light sources 211 may be implemented separately or in any combination, which is not limited in this application.

In a possible implementation, the base 23 may include an x-axis and a y-axis, the x-axis and y-axis intersecting each other at the origin. The photo detector 212 is disposed at the origin. At least two light sources 211 include a positive x-axis light source and a negative x-axis light source, the positive x-axis light source and the negative x-axis light source being fixed to a positive half axis and a negative half axis of the x-axis, respectively. At least two light sources 211 include a positive y-axis light source and a negative y-axis light source, the positive y-axis light source and the negative y-axis light source being fixed to a positive half axis and a negative half axis of the y-axis, respectively.

In a possible implementation, the positive x-axis light source and negative x-axis light source are centrally symmetrical with the origin as a center of symmetry; and/or the positive y-axis light source and negative y-axis light source are centrally symmetrical with the origin as a center of symmetry.

In a possible implementation, the positive x-axis light source may include n1 light sources, and at least two of the n1 light sources are fixed to both sides of the positive half axis of the x-axis; and/or the negative x-axis light source include n2 light sources, and at least two of the n2 light sources are fixed to both sides of the negative half axis of the x-axis, where n2 is an integer greater than 2. The positive y-axis light source may include n3 light sources, and at least two of the n3 light sources are located on both sides of the positive half axis of the y-axis, where n3 is an integer greater than 2; and/or the negative y-axis light source includes n4 light sources, and at least two of the n4 light sources are fixed to both sides of the negative half axis of the y-axis, where n4 is an integer greater than 2.

Step 1904: Fix a reflector to the top of an inner cavity of an elastomer support housing.

Exemplarily, the reflector 213 is fixed to the top of an inner cavity of an elastomer support housing 22 by glue.

In a possible implementation, a slot is disposed at the top of the inner cavity of the elastomer support housing 22, and the reflector 213 is disposed in the slot to be fixed.

It may be understood that, the foregoing method of fixing the reflector 213 may be implemented separately or in any combination, which is not limited in this application.

In a possible implementation, there is no intersection between a projection area of the reflector 213 on the base 23 and the disposing position of the light source 211. There may be one or more reflectors 213. In case a plurality of reflectors 213 are disposed, the plurality of reflectors 213 are fixed to the top of the inner cavity of the elastomer support housing according to a layout of a regular polygon, or the plurality of reflectors 213 are fixed to the top of the inner cavity of the elastomer support housing according to a layout of a circle.

Step 1906: Hermetically fix the elastomer support housing to the base so that a sensing unit is sealed in an inner cavity of the elastomer support housing.

Exemplarily, after the photo detector 212 and at least two light sources 211 are fixed on the base 23, and the reflector 213 is fixed on the top of the inner cavity of the elastomer support housing 22, the elastomer support housing 22 is sealed on the base 23 by glue or screws, so that the photo detector 212, at least two light sources 211 and the reflector 213 are sealed in the inner cavity of the elastomer support housing 22.

To sum up, the method in the embodiment offers a preparation mode for the preparation of the foregoing tactile sensor, a person skilled in the art can implement the tactile sensor by more means by choosing suitable preparation materials and preparation modes according to the actual situation.

Figure 20:
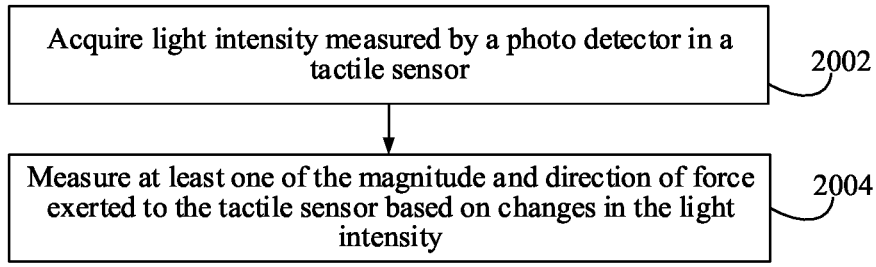
FIG. 20 is a flowchart of a detection method for a touch event according to an exemplary embodiment of this application.

Based on the description of the structure of the tactile sensor, the detection method for the touch event according to this embodiment of this application is described below. FIG. 20 is a flowchart of a detection method for a touch event according to an exemplary embodiment of this application. The method is applied to a controller connected to the tactile sensor, including:

Step 2002: Acquire light intensity measured by a photo detector in a tactile sensor.

Acquire, by a controller, light intensity measured by the photo detector 212 in the tactile sensor. The light intensity may refer to the light intensity of the light source received by the photo detector 212.

In a possible implementation, the light intensity of the light source received by the photo detector 212 refers to the light intensity of the reflected light of the light source 211 obtained by the photo detector 212, or the light intensity of the light source 211 directly received by the photo detector 212, which is limited in the embodiments of this application.

Step 2004: Measure at least one of the magnitude and direction of force exerted on the tactile sensor based on changes in the light intensity.

The measured magnitude and direction of the force exerted on the tactile sensor may refer to the magnitude or direction of press force or pull force exerted on the tactile sensor in a touch event (that is, the tactile sensor being in contact with an object) that is calculated by the controller based on the changes in the light intensity outputted by the tactile sensor.

The controller can measure the magnitude and direction of the force exerted on the tactile sensor in a touch event based on the changes in the light intensity outputted by the tactile sensor. That is, the controller may, based on the changes in the light intensity outputted by the tactile sensor, measure the magnitude and direction of the force exerted on the tactile sensor in a direction of translation, or measure the magnitude and direction of the force exerted on the tactile sensor in a direction of rotation.

To sum up, with the detection method according to the embodiment, the controller acquires the light intensity of the tactile sensor, and may calculate the magnitude and direction of the force exerted on the tactile sensor in the touch event according to the changes in the light intensity of the tactile sensor.

Figure 21:
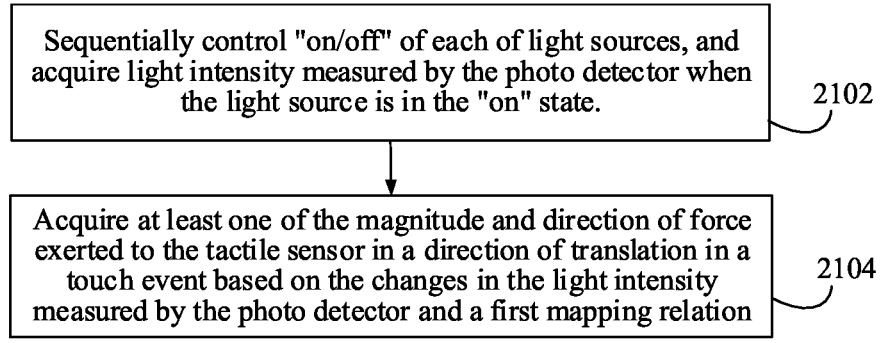
FIG. 21 is a flowchart of a detection method for force in a touch event according to an exemplary embodiment of this application.

Based on the description of the detection method for the foregoing touch event, the detection method for the force in a direction of translation in a touch event according to this embodiment of this application is described in detail below. FIG. 21 is a flowchart of a detection method for the force in a direction of translation in a touch event according to an exemplary embodiment of this application. The method is applied to a controller (e.g., a processor of a computer device) connected to the tactile sensor, the method including:

Step 2102: Sequentially control "on/off" of each of light sources, and acquire light intensity measured by the photo detector when the light source is in the "on" state.

Sequentially control "on/off" of each of the light sources 211 by the controller, and sequentially acquire light intensity measured by the photo detector 212 when the light source 211 is in the "on" state.

In a possible implementation, the controller controls "on/off" of the light source 211 with a preset frequency or period; and meanwhile, the controller acquires the light intensity received by the photo detector 212 with a preset frequency or period. Alternatively, the controller controls "on/off" of the light source with a preset frequency or period, and the controller acquires the light intensity received by the photo detector 212 within a preset time after the light source 211 is turned on, which is not limited in the embodiments of this application.

Step 2104: Acquire at least one of the magnitude and direction of force exerted on the tactile sensor in a direction of translation in the touch event based on the changes in the light intensity measured by the photo detector and a first mapping relation.

In a possible implementation, the first mapping relation may indicate a correspondence between the magnitude and direction of force exerted on the tactile sensor in a direction of translation and changes in the light intensity measured by the photo detector 212.

Exemplarily, in case a force along the x-axis is exerted on the tactile sensor, the positive x-axis light source is turned on, and the light intensity of the positive x-axis light source measured by the photo detector is acquired when the positive x-axis light source is in the "on" state; and the negative x-axis light source is turned on, and the light intensity of the negative x-axis light source measured by the photo detector is acquired when the negative x-axis light source is in the "on" state; where the magnitude and direction of force exerted on the tactile sensor in a direction of translation along the x-axis in the touch event are acquired according to a first difference value and the first mapping relation; where the first difference value may indicate a difference between the light intensity of the positive x-axis light source measured by the photo detector 212 and the light intensity of the negative x-axis light source measured by the photo detector 212. The first mapping relation may indicate a correspondence between the magnitude and direction of force exerted on the tactile sensor in a direction of translation and changes in the light intensity measured by the photo detector.

For example, in case a force along the x-axis is exerted on the tactile sensor, first, the light source c and the light source d are turned on, and the overall light intensity ($\lambda c+\lambda d$) of the light source c and the light source d is measured using the photo detector 212. Then, the light source c and the light source d are turned off, the light source h and the light source g are turned on, and the overall light intensity ($\lambda h+\lambda g$) of the light source h and the light source g is measured using the photo detector 212. By measuring the difference between the light intensity ($\lambda c+\lambda d$) and the light intensity ($\lambda h+\lambda g$), the displacement produced by the reflector 213 at the top of the inner cavity of the elastomer support housing 22 along the x-axis is obtained, and then the magnitude and direction of the force applied to the elastomer support housing 22 are obtained. in case a force along the x-axis is exerted on the tactile sensor, the correspondence between the displacement $trans_x$ produced by the reflector 213 of the tactile sensor along the x-axis and the light intensity measured by the photo detector 212 can be expressed as follows:

$$trans_x \propto \frac{(\lambda_c + \lambda_d) - (\lambda_h + \lambda_g)}{\lambda_c + \lambda_d + \lambda_h + \lambda_g}$$

Exemplarily, in case a force in a direction of translation along the y-axis is exerted on the tactile sensor, the positive y-axis light source is turned on, and the light intensity of the positive y-axis light source measured by the photo detector 212 is acquired when the positive y-axis light source is in the "on" state; the negative y-axis light source is turned on, and the light intensity of the negative y-axis light source measured by the photo detector 212 is acquired when the negative y-axis light source is in the "on" state; and the magnitude and direction of force exerted on the tactile sensor in a direction of translation along the y-axis in the touch event are acquired according to a second difference value and the first mapping relation; where the second difference value may indicate a difference between the light intensity of the positive y-axis light source measured by the photo detector 212 and the light intensity of the negative y-axis light source measured by the photo detector 212.

For example, first, the light source a and the light source b are turned on, and the overall light intensity ($\lambda a+\lambda b$) of the light source a and the light source b is measured using the photo detector 212. Then, the light source a and the light source b are turned off, the light source e and the light source f are turned on, and the overall light intensity ($\lambda e+\lambda f$) of the light source e and the light source f is measured using the photo detector 212. By measuring the difference between the light intensity ($\lambda_a+\lambda_b$) and the light intensity ($\lambda_e+\lambda_f$), the displacement produced by the reflector 213 at the top of the inner cavity of the elastomer support housing 22 along the y-axis is obtained, and then the magnitude of the force applied to the elastomer support housing 22 is obtained. in case a force in a direction of translation along the y-axis is exerted on the tactile sensor, the correspondence between the displacement transy produced by the reflector of the tactile sensor along the y-axis and the light intensity measured by the photo detector 212 can be expressed as follows:

$$trans_y \propto \frac{(\lambda_a + \lambda_b) - (\lambda_e + \lambda_f)}{\lambda_a + \lambda_b + \lambda_e + \lambda_f}$$

In a possible implementation, the light intensity of a first target light source measured by the photo detector 212 at moment i, and light intensity of the first target light source measured by the photo detector 212 at moment i+1 are acquired, where the first target light source may indicate at least one of the at least two light sources. The magnitude and direction of force exerted on the tactile sensor in the touch event are acquired according to a third difference value and the first mapping relation; where the third difference value may indicate a difference between the light intensity of the first target light source measured by the photo detector 212 at moment i and the light intensity of the first target light source measured by the photo detector at moment i+1.

Exemplarily, in case a force in a direction of translation along the z-axis is exerted on the tactile sensor, the light intensity of a first target light source measured by the photo detector 212 at moment i, and light intensity of the first target light source measured by the photo detector 212 at moment i+1 are acquired, where the first target light source indicates at least one of the at least two light sources. The magnitude and direction of force exerted on the tactile sensor in a direction of translation along the z-axis in the touch event are acquired according to a third difference value and the first mapping relation; where the third difference value may indicate a difference between the light intensity of the first target light source measured by the photo detector 212 at moment i and the light intensity of the first target light source measured by the photo detector at moment i+1.

For example, when the magnitude and direction of the force along the z-axis are to be measured, the light intensity may be measured by using at least one light source. For example, the light intensity may be measured by using only the light source c. In this case, it is required to measure the light intensity of the light source c before force in the positive direction of the z-axis is exerted on the tactile sensor, and measure the light intensity of the light source c after force in the positive direction of the z-axis is exerted on the tactile sensor. By calculating the difference in the light intensity of the light source c before and after force in the positive direction of the z-axis is exerted on the tactile sensor, the displacement produced by the reflector at the top of the inner cavity of the elastomer support housing along the z-axis is obtained, and then the magnitude of the force applied to the elastomer support housing is obtained. For example, in case a force in a direction of translation along the z-axis is exerted on the tactile sensor, the correspondence between the displacement transz produced by the reflector of the tactile sensor along the z-axis and the light intensity measured by the photo detector 212 can be expressed as follows:

$$trans_z \propto \frac{\lambda_{c1} - \lambda_{c2}}{\lambda_{c1} + \lambda_{c2}}$$

To sum up, according to the detection method of the embodiment, the controller receives the light intensity of the light source at a specific position through the photo detector, and calculates the magnitude and direction of the force exerted on the tactile sensor in a direction of translation in the touch event based on the correspondence between the light intensity of the corresponding light source measured by the photo detector and the first mapping relation. In this way, the tactile sensor using the detection method can measure the magnitude and direction of the force exerted on the tactile sensor in a direction of translation in the touch event.

Figure 22:
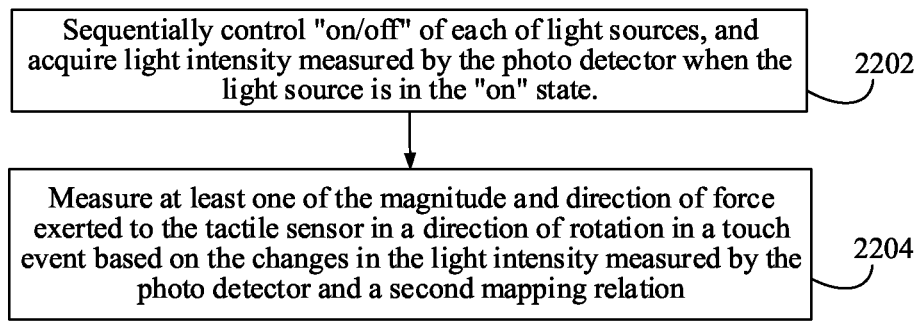
FIG. 22 is a flowchart of a detection method for force in another touch event according to an exemplary embodiment of this application.

Based on the description of the detection method for the foregoing touch event, the detection method for the force in a direction of rotation in a touch event according to this embodiment of this application is described in detail below. FIG. 22 is a flowchart of a detection method for the force in a direction of rotation in a touch event according to an exemplary embodiment of this application. The method is applied to a controller (e.g., a processor of a computer device) connected to the tactile sensor, the method including:

Step 2202: Sequentially control "on/off" of each of light sources, and acquire light intensity measured by the photo detector when the light source is in the "on" state.

Sequentially control "on/off" of each of light sources 211 by the controller, and sequentially acquire light intensity 212 measured by the photo detector when the light source is in the "on" state.

In a possible implementation, the controller controls "on/off" of the light source 211 with a preset frequency or period; and meanwhile, the controller acquires the light intensity received by the photo detector 212 with a preset frequency or period. Alternatively, the controller controls "on/off" of the light source 211 with a preset frequency or period, and the controller acquires the light intensity received by the photo detector 212 within a preset time after the light source 211 is turned on, which is not limited in the embodiments of this application.

Step 2204: Measure at least one of the magnitude and direction of force exerted on the tactile sensor in a direction of rotation in the touch event based on the changes in the light intensity measured by the photo detector and a second mapping relation.

In a possible implementation, the second mapping relation may indicate a correspondence between the magnitude and direction of force exerted on the tactile sensor in a direction of rotation and changes in the light intensity measured by the photo detector 212.

Exemplarily, in case a force in a direction of rotation about the x-axis is exerted on the tactile sensor, the first x-axis light source is turned on, and the light intensity of the first x-axis light source measured by the photo detector 212 is acquired when the first x-axis light source is in the "on" state; and the second x-axis light source is turned on, and the light intensity of the second x-axis light source measured by the photo detector 212 is acquired when the second x-axis light source is in the "on" state.

The magnitude and direction of force exerted on the tactile sensor in a direction of rotation about the x-axis in the touch event are acquired according to a fourth difference value and the second mapping relation.

The fourth difference value may indicate a difference between the light intensity of the first x-axis light source measured by the photo detector 212 and the light intensity of the second x-axis light source measured by the photo detector 212. The first x-axis light source includes a first positive x-axis light source, and the second x-axis light source includes a second positive x-axis light source; or the first x-axis light source includes a first negative x-axis light source, and the second x-axis light source includes a second negative x-axis light source; or the first x-axis light source includes a first positive x-axis light source and a first negative x-axis light source, and the second x-axis light source includes a second positive x-axis light source and a second negative x-axis light source.

For example, in case a force in a direction of rotation about the x-axis is exerted on the tactile sensor, first, the light source g and the light source d are turned on, and the overall light intensity ($\lambda g+\lambda d$) of the light source g and the light source d is measured using the photo detector 212. Then, the light source g and the light source d are turned off, the light source h and the light source g are turned on, and the overall light intensity ($\lambda h+\lambda c$) of the light source h and the light source c is measured using the photo detector. By measuring the difference between the light intensity ($\lambda g+\lambda d$) and the light intensity ($\lambda h+\lambda c$), the rotational displacement or angle produced by the reflector 213 at the top of the inner cavity of the elastomer support housing 22 about the x-axis is obtained, and then the magnitude of the force applied to the elastomer support housing 22 is obtained. For example, in case a torque about the x-axis is exerted on the tactile sensor, the correspondence between the displacement revolx produced by the rotation of the reflector 213 of the tactile sensor about the x-axis and the light intensity measured by the photo detector 212 can be expressed as follows:

$$revol_x \propto \frac{(\lambda_g + \lambda_d) - (\lambda_h + \lambda_c)}{\lambda_c + \lambda_d + \lambda_h + \lambda_g}$$

Exemplarily, in case a force in a direction of rotation about the y-axis is exerted on the tactile sensor, the first y-axis light source is turned on, and the light intensity of the first y-axis light source measured by the photo detector 212 is acquired when the first y-axis light source is in the "on" state; and the second y-axis light source is turned on, and the light intensity of the second y-axis light source measured by the photo detector 212 is acquired when the second y-axis light source is in the "on" state.

The magnitude and direction of force exerted on the tactile sensor in a direction of rotation about the x-axis in the touch event are acquired according to a fifth difference value and the second mapping relation.

The fifth difference value may indicate a difference between the light intensity of the first y-axis light source measured by the photo detector 212 and the light intensity of the second y-axis light source measured by the photo detector 212. The first y-axis light source includes a first positive y-axis light source, and the second y-axis light source includes a second positive y-axis light source; or the first y-axis light source includes a first negative y-axis light source, and the second y-axis light source includes a second negative y-axis light source; or the first y-axis light source includes a first positive y-axis light source and a first negative y-axis light source, and the second y-axis light source includes a second positive y-axis light source and a second negative y-axis light source.

For example, first, the light source a and the light source f are turned on, and the overall light intensity ($\lambda a+\lambda f$) of the light source a and the light source f is measured using the photo detector 212. Then, the light source a and the light source f are turned off, the light source e and the light source b are turned on, and the overall light intensity ($\lambda e+\lambda b$) of the light source e and the light source b is measured using the photo detector 212. By measuring the difference between the light intensity ($\lambda a+\lambda f$) and the light intensity ($\lambda e+\lambda b$), the rotational displacement or angle produced by the reflector 213 at the top of the inner cavity of the elastomer support housing 22 about the y-axis is obtained, and then the magnitude of the force applied to the elastomer support housing 22 is obtained. For example, in case a force in a direction of rotation about the y-axis is exerted on the tactile sensor, the correspondence between the displacement revoly produced by the rotation of the reflector 213 of the tactile sensor about the y-axis and the light intensity measured by the photo detector 212 can be expressed as follows:

$$revol_y \propto \frac{(\lambda_a + \lambda_f) - (\lambda_e + \lambda_b)}{\lambda_a + \lambda_b + \lambda_e + \lambda_f}$$

Exemplarily, in case a force in a direction of rotation about the z-axis is exerted on the tactile sensor, the second target light source is turned on, and the light intensity of the second target light source measured by the photo detector is acquired when the second target light source is in the "on" state; and the third target light source is turned on, and the light intensity of the third target light source measured by the photo detector is acquired when the third target light source is in the "on" state; where the second target light source is any one of the at least two light sources, and the third target light source may be a light source of the at least two light sources other than the second target light source.

The magnitude and direction of force exerted on the tactile sensor in a direction of rotation about the z-axis in the touch event are acquired according to a sixth difference value and the second mapping relation.

The sixth difference value may indicate a difference between the light intensity of the second target light source measured by the photo detector 212 and the light intensity of the third target light source measured by the photo detector 212.

For example, first, the light source b, light source d, light source f and light source h are turned on, and the overall light intensity ($\lambda b+\lambda d+\lambda h+\lambda f$) of the light source b, light source d, light source f and light source h is measured using the photo detector 212. Then, the light source b, light source d, light source f and light source h are turned off, the light source a, light source c, light source e and the light source g are turned on, and the overall light intensity ($\lambda a+\lambda c+\lambda e+\lambda g$) of the light source a, light source c, light source e and the light source g is measured using the photo detector 212. By measuring the difference between the light intensity ($\lambda b+\lambda d+\lambda+\lambda f$) and the light intensity ($\lambda a+\lambda c+\lambda e+\lambda g$), the rotational displacement or angle produced by the reflector 213 at the top of the inner cavity of the elastomer support housing 22 about the z-axis is obtained, and then the magnitude of the force applied to the elastomer support housing 22 is obtained. For example, in case a force in a direction of rotation about the z-axis is exerted on the tactile sensor, the correspondence between the displacement revolz produced by the rotation of the reflector 213 of the tactile sensor about the z-axis and the light intensity measured by the photo detector 212 can be expressed as follows:

$$revol_z \propto \frac{(\lambda_a + \lambda_c + \lambda_e + \lambda_g) - (\lambda_b + \lambda_d + \lambda_h + \lambda_f)}{\lambda_a + \lambda_b + \lambda_c + \lambda_d + \lambda_e + \lambda_f + \lambda_g + \lambda_h}$$

Exemplarily, the light intensity of a fourth target light source measured by the photo detector at moment i, and the light intensity of the fourth target light source measured by the photo detector at moment i+1 are acquired, where the fourth target light source may indicate at least one of the at least two light sources.

The magnitude and direction of force exerted on the tactile sensor in a direction of rotation in the touch event are acquired according to a seventh difference value and the second mapping relation. The seventh difference value may indicate a difference between the light intensity of the fourth target light source measured by the photo detector at moment i and the light intensity of the fourth target light source measured by the photo detector at moment i+1.

For example, when the magnitude and direction of the force about the z-axis are to be measured, the light intensity may be measured by using at least one light source. For example, the light intensity may be measured by using only the light source c. In this case, it is required to measure the light intensity of the light source c before force in a direction of clockwise rotation about the z-axis is exerted on the tactile sensor, and measure the light intensity of the light source c after force in a direction of clockwise rotation about the z-axis is exerted on the tactile sensor. By calculating the difference in the light intensity of the light source c before and after force in a direction of clockwise rotation about the z-axis is exerted on the tactile sensor, the displacement produced by the reflector at the top of the inner cavity of the elastomer support housing along the z-axis is obtained, and then the magnitude of the force applied to the elastomer support housing is obtained.

To sum up, according to the detection method of the embodiment, the controller receives the light intensity of the light source at a specific position through the photo detector, and the controller calculates the magnitude and direction of the force exerted on the tactile sensor in a direction of rotation in the touch event according to the correspondence between the changes in the light intensity of the corresponding light source measured by the photo detector and the second mapping relation. In this way, the tactile sensor using the detection method can measure the magnitude and direction of the force exerted on the tactile sensor in a direction of rotation in the touch event.

Figure 23:
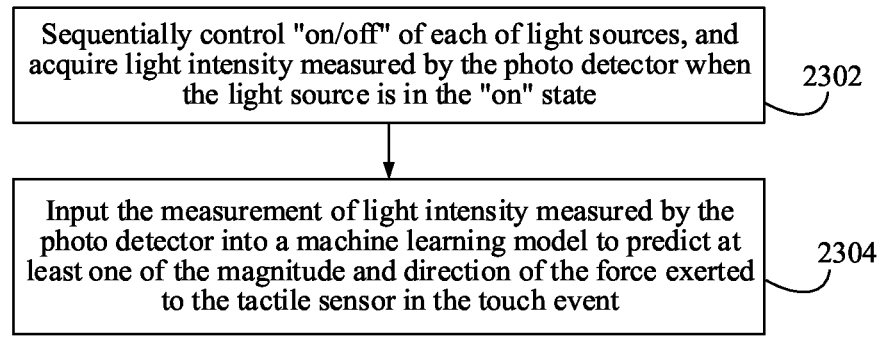
FIG. 23 is a flowchart of force in a detection method for force in still another touch event according to an exemplary embodiment of this application.

Based on the description of the detection method for the foregoing touch event, the detection method for the force in a direction of rotation and/or direction of translation in a touch event according to this embodiment of this application is described in detail below. FIG. 23 is a flowchart of a detection method for the force in a direction of rotation and/or direction of translation in a touch event according to an exemplary embodiment of this application. The method is applied to a controller (e.g., a processor of a computer device) connected to the tactile sensor, the method including:

Step 2302: Sequentially control "on/off" of each of light sources, and acquire light intensity measured by the photo detector when the light source is in the "on" state.

Sequentially control "on/off" of each of the light sources 211 by the controller, and sequentially acquire light intensity 212 received by the photo detector when the light source is in the "on" state.

In a possible implementation, the controller controls "on/off" of the light source 211 with a preset frequency or period; and meanwhile, the controller acquires the light intensity received by the photo detector 212 with a preset frequency or period. Alternatively, the controller controls "on/off" of the light source with a preset frequency or period, and the controller acquires the light intensity received by the photo detector 212 within a preset time after the light source is turned on, which is not limited in the embodiments of this application.

Step 2304: Input the light intensity measured by the photo detector into a machine learning model to predict at least one of the magnitude and direction of the force exerted on the tactile sensor in the touch event.

In a possible implementation, the machine learning model is trained by a computer device according to a correspondence between the magnitude and direction of force exerted on the tactile sensor and changes in the light intensity measured by the photo detector 212.

Exemplarily, the controller receives the light intensity of light sources at specific positions through the photo detector 212, such as the light source c, the light source d, the light source h, and the light source g at the specific positions. The photo detector 212 receives light intensity $\lambda c$, light intensity $\lambda d$, light intensity $\lambda h$ and light intensity $\lambda g$ of the corresponding light sources 211, respectively. The controller inputs the measured light intensity into the machine learning model, and the machine learning model calculates the magnitude and direction of the force exerted on the tactile sensor.

In a possible implementation, the machine learning model involves the following training modes: (1) Acquire training samples. The training samples include sample force and sample tactile results. The sample force refers to the known force acting on the tactile sensor, that is, a direction and magnitude of the known force; and the sample tactile results refer to the light intensity of the corresponding light source measured by the photo detector in case the tactile sensor is under the action of the sample force. (2) Acquire predicted tactile results. Input the sample force into the machine learning model to obtain the predicted tactile results, that is, predicted light intensity. (3) Obtain error loss. Obtain error loss by calculating an error between the predicted tactile results and the sample tactile results. (4) Train, by an error backpropagation algorithm, the machine learning model according to the error loss, so as to obtain the trained machine learning model.

To sum up, according to the detection method of the embodiment, the controller receives the light intensity of the light source at a specific position through the photo detector, and the controller inputs the light intensity of the corresponding light source received by the photo detector into the machine learning model; the machine learning model calculates the magnitude and direction of the force exerted on the tactile sensor. In this way, the tactile sensor using the detection method can measure the magnitude and direction of the force exerted on the tactile sensor in a direction of rotation and/or direction of translation in the touch event.

Figure 24:
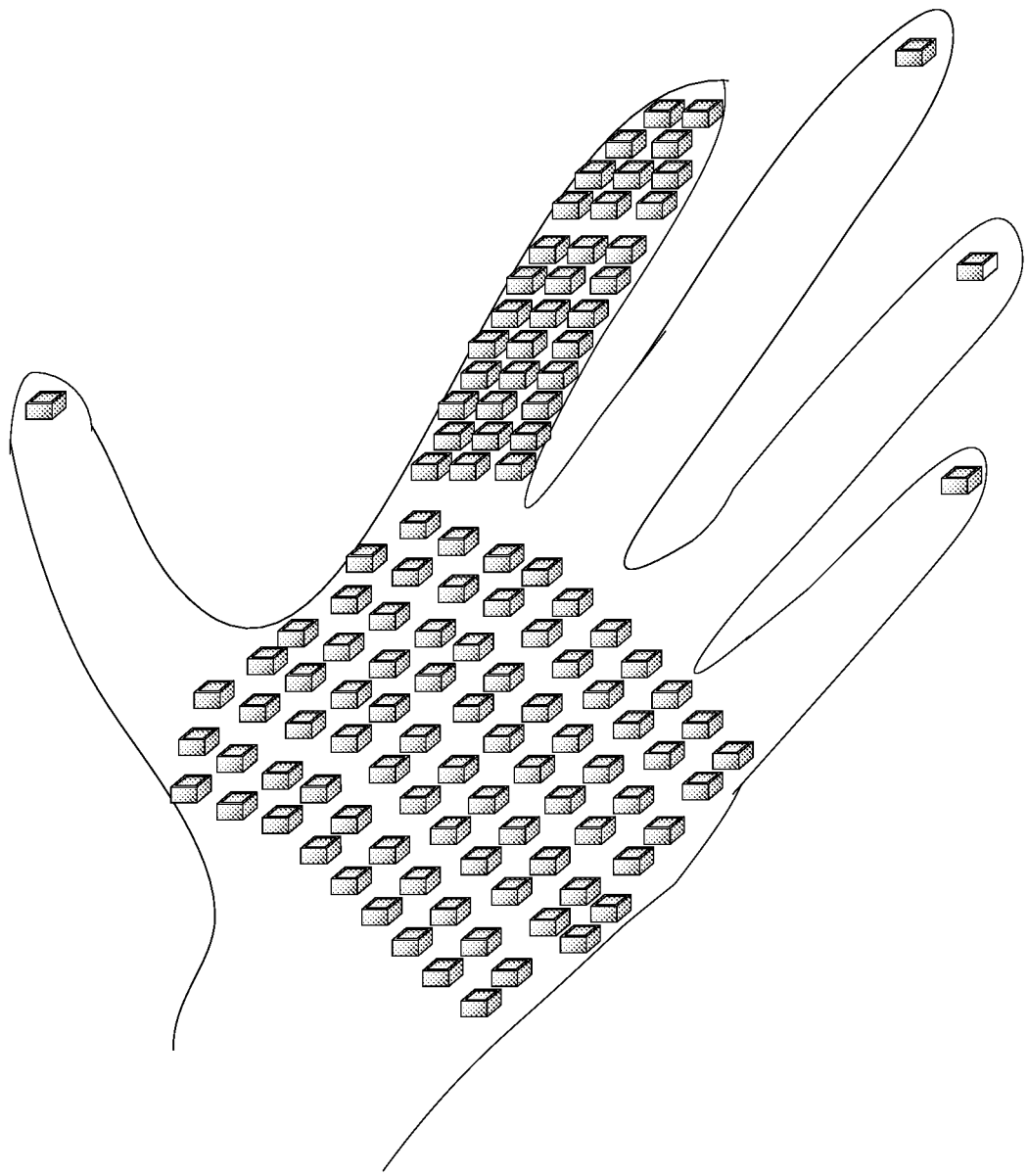
FIG. 24 is a schematic diagram of an electronic skin according to an exemplary embodiment of this application.

Based on the description of the above tactile sensor and the detection method for a touch event, FIG. 24 shows a schematic diagram of an electronic skin.

Exemplarily, the electronic skin is covered with a tactile sensor array including at least two of the foregoing tactile sensors.

For example, as shown in FIG. 24, by attaching the electronic skin to the manipulator, the manipulator can collect tactile signals from the motion of gripping an object and give feedback to the controller. For example, the manipulator gives feedback to the controller on whether the object slipped in the manipulator at the time of making initial contact with the object. The manipulator can be configured to adjust the grip force, so as to maintain the optimal grip force without crushing the object. The tactile sensor on the manipulator can provide the information about the force in a direction of rotation, that is, torque information, which allows the controller to better estimate the posture of the object in the hand.

In a possible implementation, the arrangement of the electronic skin may be adjusted according to the shape of the manipulator.

To sum up, with the electronic skin according to this embodiment, the tactile sensor array covering the electronic skin achieves multi-directional sensing of the magnitude and direction of the force in a direction of rotation and/or direction of translation exerted on the tactile sensor, thereby providing accurate sensing and feedback.

Based on the foregoing tactile sensor and the detection method for a touch event, an exemplary embodiment of this application provides a robot, the robot being covered with the above tactile sensor or the above electronic skin at a preset position and including a manipulator, such as: a hand part, where the manipulator is configured to grab objects, and the manipulator is covered with the foregoing tactile sensor or the electronic skin.

Figure 25:
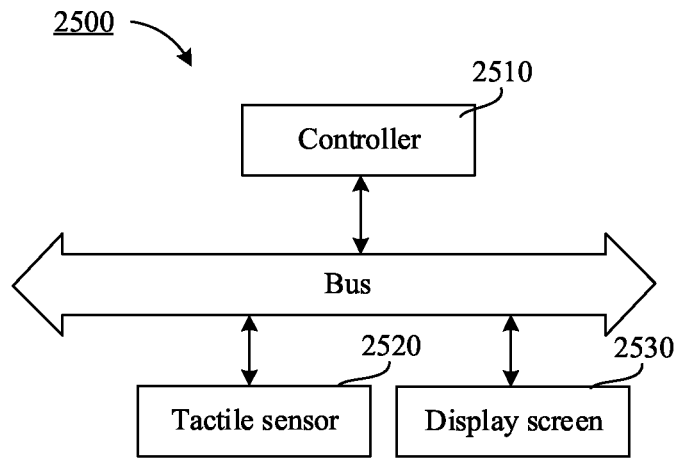
FIG. 25 is a schematic structural diagram of a sensing device according to an exemplary embodiment of this application.

Based on the foregoing tactile sensor and the detection method for a touch event, an exemplary embodiment of this application provides a structural block diagram of a sensing device. As shown in FIG. 25, the sensing device 2500 includes: at least one foregoing tactile sensor 2520 and a controller 2510 connected to the tactile sensor 2520 and executing the foregoing detection method for a touch event.

In a possible implementation, the intelligent device 2500 further includes a display screen 2530.

The tactile sensor 2520 is configured to detect a touch event. In a possible implementation, the tactile sensor 2520 is implemented as a tactile sensor as shown in FIG. 2.

In a possible implementation, the embodiments provide a computer-readable storage medium connected to the tactile sensor according to the foregoing embodiment, and storing at least one instruction, the at least one instruction being loaded and executed by the processor to implement the foregoing detection method for a touch event.

In a possible implementation, the computer-readable storage medium may include: a read-only memory (ROM), a random access memory (RAM), a solid state drive (SSD), an optical disc, or the like. The RAM may include a resistance random access memory (ReRAM) and a dynamic random access memory (DRAM). The sequence numbers of the foregoing embodiments of this application are merely for description purpose but do not imply the preference among the embodiments.

A person skilled in the art may understand that all or some of the steps of the foregoing embodiments may be implemented by hardware, or may be implemented by a program instructing relevant hardware. The program may be stored in a computer-readable storage medium. The foregoing storage medium may be a read-only memory, a magnetic disk, an optical disc, or the like.

It is to be understood that, The application scenarios of the foregoing tactile sensor include at least one of the following:

First, the tactile sensor is applied to an application scenario of remote control. In this scenario, with the remote control over the manipulator, the tactile sensor on the manipulator feeds the magnitude and direction of the force exerted on the manipulator back to a tactile rendering device. The tactile rendering device feeds the force rendering result of the manipulator back to an operator, so that the operator can be clear about the magnitude and direction of the force exerted on the manipulator through the force rendering result.

Second, the tactile sensor is applied to a scenario of a self-protection system of the intelligent robot. In this scenario, the tactile sensor is arranged on the body surface of the intelligent robot, and can sense the external environment in real time and protect its own system. The tactile sensor has high sensitivity to pressure, and can trigger a self-protection switch of the intelligent robot to cut off power or implement other self-protection behavior when the intelligent robot is impacted to a certain degree, that is, when the detected pressure exceeds a certain threshold range.

Third, the tactile sensor is applied to the scenario of measurement and diagnosis tools. In this scenario, the tactile sensor is arranged on the surface of the manipulator, and whether the force required to complete a task is reasonable is determined based on the information on the force fed back when the manipulator is operated to complete the task. For example, the torque exerted by the manipulator's fingertips is measured when the manipulator is operated to pull the plug, which allows for the understanding of whether the torque required to complete the task is reasonable.

It is to be understood that, regarding the above application scenarios, the application scenario of remote control, the scenario of a self-protection system of the intelligent robot and the scenario of measurement and diagnosis tools are taken as examples for description. The tactile sensor can also be applied to other scenarios where the magnitude and/or direction of the force need to be determined, which is not limited in the embodiments of this application.

Figure 26:
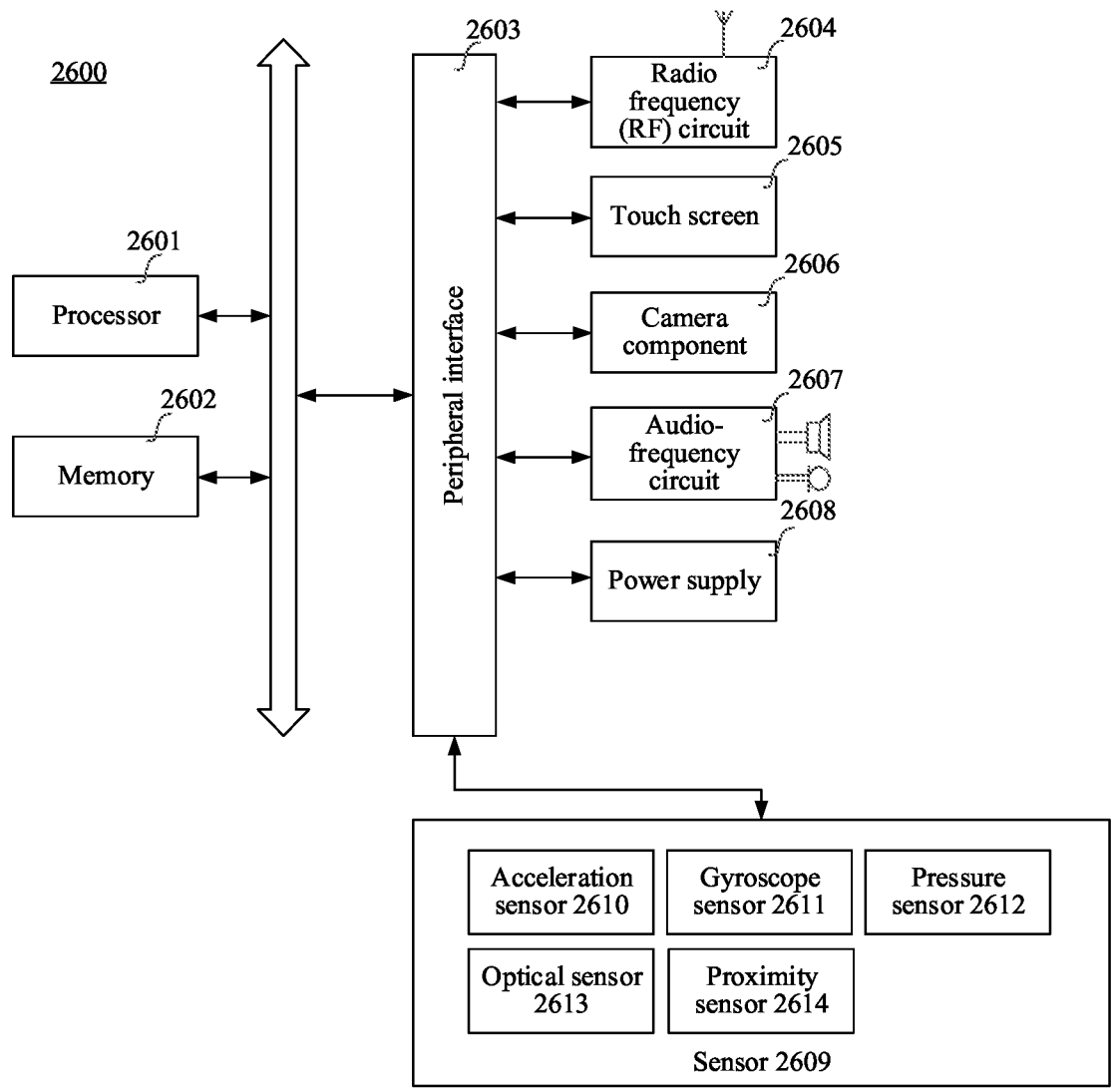
FIG. 26 is a schematic structural diagram of a computer device according to an exemplary embodiment of this application.

FIG. 26 shows a structural block diagram of a computer device 2600 according to an exemplary embodiment of this application. The computer device 2600 may be a portable mobile terminal, such as: a smartphone, a tablet computer, a Moving Picture Experts Group Audio Layer III (MP3) player and a Moving Picture Experts Group Audio Layer IV (MP4) player. The computer device 2600 may also be referred to as user equipment, a portable terminal or the like.

Generally, the computer device 2600 includes: a processor 2601 and a memory 2602, the processor 2601 being connected to the tactile sensor according to the foregoing embodiment.

The processor 2601 may include one or more processing cores, for example, a 4-core processor or an 8-core processor. The processor 2601 may be implemented in at least one hardware form of a digital signal processor (DSP), a field-programmable gate array (FPGA), and a programmable logic array (PLA). The processor 2601 may also include a main processor and a coprocessor. The main processor is a processor configured to process data in an awake state, and is also referred to as a central processing unit (CPU). The coprocessor is a low power consumption processor configured to process the data in a standby state. In some embodiments, the processor 2601 may be integrated with a graphics processing unit (GPU). The GPU is configured to render and draw content that needs to be displayed on a display screen. In some embodiments, the processor 2601 may further include an artificial intelligence (AI) processor. The AI processor is configured to process computing operations related to machine learning.

The memory 2602 may include one or more computer-readable storage media. The computer-readable storage medium may be tangible and non-transient. The memory 2602 may further include a high-speed random access memory and a nonvolatile memory, for example, one or more disk storage devices or flash storage devices. In some embodiments, the non-transitory computer-readable storage medium in the memory 2602 is configured to store at least one instruction, and the at least one instruction is configured to be executed by the processor 2601 to implement the detection method for a touch event according to this application.

In some embodiments, the computer device 2600 may further include: a peripheral interface 2603 and at least one peripheral. Specifically, the peripheral includes: at least one of a radio frequency (RF) circuit 2604, a touch display 2605, a camera 2606, an audio circuit 2607 and a power supply 2608.

In some embodiments, the computer device 2600 further includes one or more sensors 2609. The one or more sensors 2609 include, but not limited to: an acceleration sensor 2610, a gyroscope sensor 2611, a pressure sensor 2612, an optical sensor 2613 and a proximity sensor 2614.

A person skilled in the art may understand that the structure shown in FIG. 26 constitutes no limitation to the computer device 2600, and the computer device may include more or fewer components than those shown in the figure, or some components may be combined, or a different component deployment may be used.

It is to be understood that, the "plurality of" mentioned herein indicates two or more. "And/or" describes an association relationship for describing associated objects, and represents that three relationships may exist. For example, A and/or B may represent the following three cases: Only A exists, both A and B exist, and only B exists. The character "/" in this specification generally indicates an "or" relationship between the associated objects.

The foregoing descriptions are merely embodiments of this application, but are not intended to limit this application. Any modification, equivalent replacement, or improvement made within the spirit and principle of this application shall fall within the protection scope of this application.

What is claimed is:

1. A tactile sensor comprising: a sensing unit, an elastomer support housing and a base;
   the sensing unit being disposed in an inner cavity enclosed by the elastomer support housing and the base; and
   the sensing unit comprises at least eight light sources, a photo detector and a reflector, the photo detector being disposed on the base, the at least eight light sources being evenly disposed around an octagon-shaped periphery of the photo detector on the base with the photo detector as a center of symmetry, and the reflector being disposed at a top of the inner cavity of the elastomer support housing,
   wherein the photo detector is configured to measure a change in light intensity of light from each of the light sources reflected by the reflector separately by turning on/off the light source when a force is applied to the elastomer support housing and the changes in the light intensity of the reflected light of the at least eight light sources are then configured for determining magnitude and direction of the force in six degrees of freedom.

2. The tactile sensor according to claim 1, wherein the base comprises an x-axis and a y-axis which intersect at an origin on the base;
   the photo detector is disposed at the origin; and
   the at least eight light sources comprise two positive x-axis light sources, two negative x-axis light sources, two positive y-axis light sources and two negative y-axis light sources, wherein the two positive x-axis light sources are located on a positive half axis of the x-axis, the two negative x-axis light sources are located on a negative half axis of the x-axis, the two positive y-axis light sources are located on a positive half axis of the y-axis, and the two negative y-axis light sources are located on a negative half axis of the y-axis.

3. The tactile sensor according to claim 1, wherein no intersection exists between a projection area of the reflector on the base and disposing positions of the at least eight light sources.

4. The tactile sensor according to claim 1, wherein the elastomer support housing is of an integral structure, and is made of a silicone material.

5. The tactile sensor according to claim 1, wherein the elastomer support housing comprises a rigid plate and a deformable support, the rigid plate is connected to the base through the deformable support, and the reflector is fixed to a lower surface of the rigid plate.

6. An electronic skin, the electronic skin being covered with a tactile sensor array comprising at least two tactile sensors according to claim 1.

7. A robot, the robot being covered with the tactile sensor according to claim 1 at a preset position.

* * * * *